US006251671B1

(12) United States Patent
Hogan et al.

(10) Patent No.: US 6,251,671 B1
(45) Date of Patent: *Jun. 26, 2001

(54) COMPOSITIONS AND METHODS OF MAKING EMBRYONIC STEM CELLS

(75) Inventors: Brigid L. M. Hogan, Brentwood; Guang-Quan Zhao, Nashville, both of TN (US)

(73) Assignee: Vanderbilt University, Nashville, TN (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/808,346

(22) Filed: Feb. 28, 1997

Related U.S. Application Data

(60) Provisional application No. 60/012,386, filed on Feb. 28, 1996, and provisional application No. 60/012,384, filed on Feb. 28, 1996.

(51) Int. Cl.[7] .............................. C12N 5/00; C12N 5/02
(52) U.S. Cl. .......................... 435/384; 435/385; 435/386; 435/387
(58) Field of Search .................................. 435/384, 385, 435/386, 387

(56) References Cited

U.S. PATENT DOCUMENTS

| | | |
|---|---|---|
| 5,166,190 | 11/1992 | Mather et al. . |
| 5,334,702 | 8/1994 | Green et al. . |
| 5,453,357 | 9/1995 | Hogan . |
| 5,605,803 | 2/1997 | Herr et al. . |
| 5,690,926 * | 11/1997 | Hogan ................................. 424/93.1 |

FOREIGN PATENT DOCUMENTS

93/17032   9/1993   (WO) .

OTHER PUBLICATIONS

Haneji et al., "Differential Effects of Epidermal Growth Factor on the Differentiation of Type A Spermatogonia in Adult Mouse Cryptorchid Testes In–Vitro", J. Endocrinol. 128 (3) : 383–388 (1991).*
Parvinen et al., "In–Vitro Stimulation of Stage–Specific DNA Synthesis in Rat Seminiferous Tublule Segments by Interleukin 1–alpha" Endocrinology 129 (3): 1614–20 (1991).*
Rossi et al., "Follicle–Stimulating Hormone Induction of Steel Factor SLF mRNA in Mouse Sertoli Cells and Stimulation of DNA Synthesis in Spermatogonia by Soluble SLF", Dev. Biol. 155 (1) : 68–74 (1993).*
Meyer et al., "Serum basic fibroblast growth factor in men with and without prostate carcinoma", Cancer 76 (11): 2304–11 (1995).*
Bergmann et al., Partial purification of a fibroblast growth factor from calf and horse serum which utilizes the thrombin receptor system. J. Cell Biol. 97 (5 part 2): 394A (1983).*
Green, 1968, *J. Exp. Zool.* 167:129–150.
Billington, 1971, *Adv. Reprod. Physiol.* 5:27–66.
Finn, 1971, *Adv. Reprod. Physiol.* 5:1–26.
Steinberger et al., 1976, *Endocrinology* 99:918–921.
Sanger et al., 1977, *Proc. Natl. Acad. Sci. USA* 74:5463–5467.
Wright et al., 1986, *Biol. Reprod.* 35:761–772.
Bicsak et al., 1987, *Mol. Cell. Endocrinol.* 49:211–217.
Allan et al., 1987, In *Perspectives on Mammalian Cell Death*, (Potten, C. S. 1Ed.), Oxford University Press, London. pp. 229–258.
Frohman et al., 1988, *Proc. Natl. Acad. Sci. USA* 85:8998–9002.
Handel et al., 1988, *Gamete Res.* 21:409–423.
Meunier et al., 1988, *Proc. Natl. Acad. Sci. USA* 85:247–251.
Bertchtold, 1989, *Nucleic Acids Res.* 17: 453.
Bhasin et al., 1989, Endocrinology 124:987–991.
Loh et al., 1989, *Science* 243:217–220.
Cate et al., 1990, In *Peptide Growth Factors and Their Receptor*, (Sporn et al. Eds.), Springer–Verlag, Berlin, vol. 2, pp. 179–210.
Johnson et al., 1990, *Nature* 346:858–861.
Lyons et al., 1990, *Development* 109:833–844.
Russell et al. 1990, In *Histological and Histopathological Evaluation of the Testis*, Cache River Press, Clearwater, Fl., pp. 119–161.
Yagi et al., 1990, *Proc. Natl. Acad. Sci. USA* 87:9918–9922.
Allan et al., 1992, *Cell Prolif.* 25:241–250.
Rudnicki, et al., 1992, *Cell* 71:383–390.
Gavrieli et al., 1992, *J. Cell. Biol.* 119:493–501.
Jones et al., 1992, *Development* 115:639–647.
Kingsley et al., 1992, *Cell* 71:399–410.
Matzuk et al., 1992, *Nature* 360:313–319.
Özkaynak et al., 1992, *J. Biol. Chem.* 267:25220–25227.
Hughes, et al., 1995, *Endo* 136:2671–2677.
Bellve, 1993,In *Methods in Enzymology* 225:84–113.
Evans et al., 1993, *Dev. Biol.* 159, 485–499.
Murray et al., 1993, *J. Cell. Biochem.* 53:51–60.
Wright et al., 1993, In *Cell and Molecular Biology of the Testis*, (Eds.: Desjardins et al.), pp.377–399, Oxford Univ. Press NY.

(List continued on next page.)

Primary Examiner—Sandra E. Saucier
(74) Attorney, Agent, or Firm—Akin, Gump, Strauss, Hauer & Feld, L.L.P.

(57) ABSTRACT

The invention relates to cell proliferation, cell differentiation, male infertility, male fertility and to compositions and methods involved therein. Also methods of culturing spermatogonial stem cells with bone morphogenetic protein 8 are disclosed.

9 Claims, 22 Drawing Sheets

OTHER PUBLICATIONS

Zhao et al., 1993, *Proc. Natl. Acad. Sci. USA* 90:8633–8637.
Zhou et al., 1993, *Nature* 361:543–547.
Behringer et al., 1994, *Cell* 79, 415–425.
Conlon et al., 1994, *Development* 120:1919–1928.
Cross et al., 1994, *Science* 266, 1508–1518.
Graff et al., 1994, *Cell* 79:169–179.
Harland, 1994, *Proc. Natl. Acad. Sci. USA* 91:10243–10246.
Vassalli et al., 1994, Genes Dev. 8: 414–427.
Janatpour et al., 1994 Mol.Biol.Cell. 5:(suppl., 453a), 2636.
King et al., 1994, *Dev. Biol.* 116:112–122.
Kingsley, 1994, *Genes Dev.* 8:133–146.
Massague et al., 1994, *Trends Cell Biol.* 4:172–178.
Rowe et al., 1994, *Mamm. Genome* 5:253–274.
Storm et al., 1994, *Nature* 368:639–643.

\* cited by examiner

```
MAMRPGPIWLLGLALCALGGHGPRPPHTCPQRRLGARERRDMQREILAVLGLPGRPRPRAQPAAARQPASAPLFMLDLY      80
|| : ||   |||||||||||||  ||   |||   ||||||  :||  |||||  |  :  ||   ||||||||||||
MAARPGLIWLLGLALCVLGGGHLSHPPHVFPQRRLGVREPRDMQREIREVLGLPGRPRSRAPVGAAQQPASAPLFMLDLY

HAMTDDDDGPPQAHLGRADLVMSFVNMVERDRTLGYQEPHWKEFHFDLTQIPAGEAVTAAEFRIYKEPSTHPLNTTLHI    160
: ||| ||  ||||  ||||||||||||||||||||||||:||||||||||||||||||||||||||||||||||||:||
RAMTDDSGGTPQPHLDRADLIMSFVNIVERDRTLGYQEPHWKEFHFDLTQIPAGEAVTAAEFRIYKEPSTHPLNTTFHI

SMFEVVQEHSNRESDLFFLDLQTLRSGDEGWLVLDITAASDRWLLNHHKDLGLRLYVETADGHSMDPGLAGLLGRQAPRS   240
|||||||||||||||||:||||||||||||||||||||||||||||||||||||||||||| |||||||||||||||
SMFEVVQEHSNRESDLSFLDLQTLRSGDEGWLVLDITAASDRWLLNHHKDLGLRLYVETEDGHGIDPGLAGLLGRQAPRS

RQPFMVTFEFRASQSPVRAPRAARPLKRRQPKKTNELPHPNKLPGIFDDGHGSRGREVCRRHELYVSFRDLGWLDWVIAPQ  320
||||||  ||||:|||||||   ||||:  :  ||| | :||||| | ||||| |||||| |||||||||||| ||||||
RQPFMVGFFRANQSPVRAPRTARPLKKKQLNQINQLPHSNKHLGILDDGHGSHGREVCRIGELYVSFRDLGWLDSVIAPQ

GYSAYYCEGECAFPLDSCMNATNHAILQSLVHLMKPDVVPKACCAPTKLSATSVLYYDSSNNVILRKHRNMVVKACGCH   399
||||||| ||| |  |:||:||||| ||| ||||||| ||| ::||| ||| | |||| |:|  ||||||| ||||||
GYSAYYCAGECIYPLNSCMNSTNHATMQALVHLMKPDIIPKVCCVPTELSAISLLYYDRNNNVILRRERNMVVQACGCH
```

FIG. 1

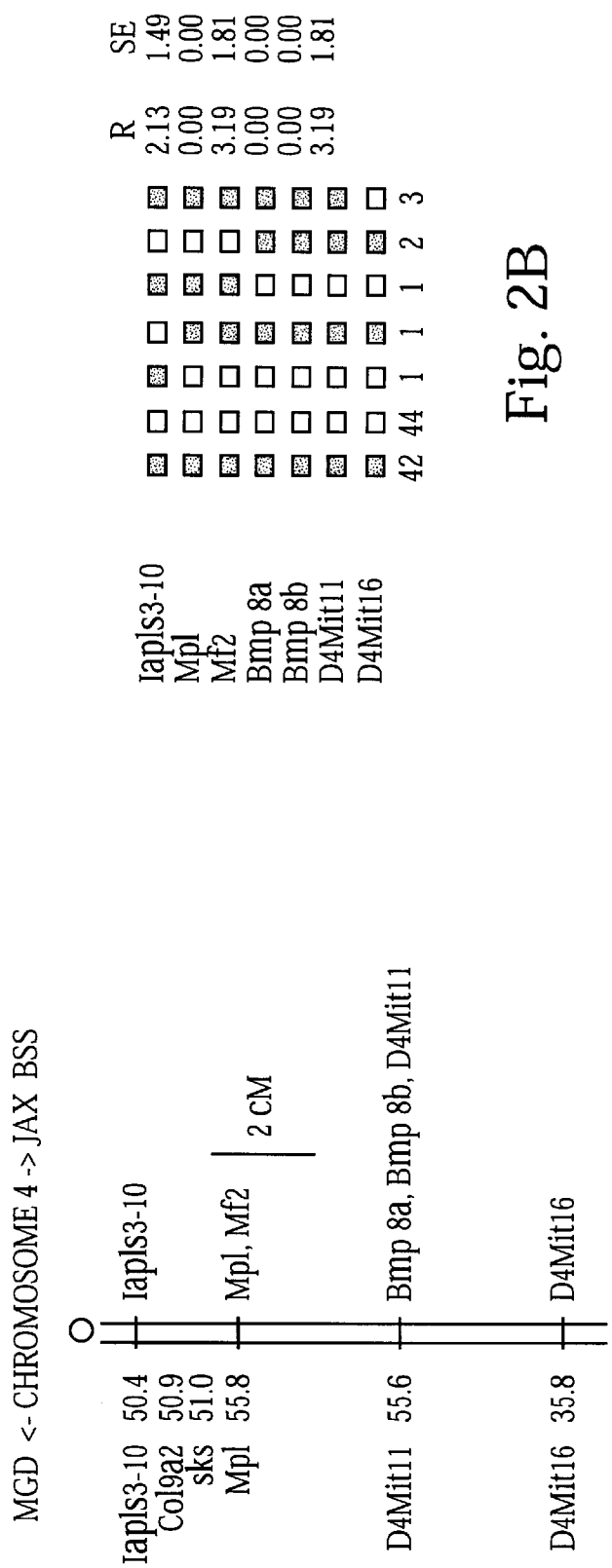

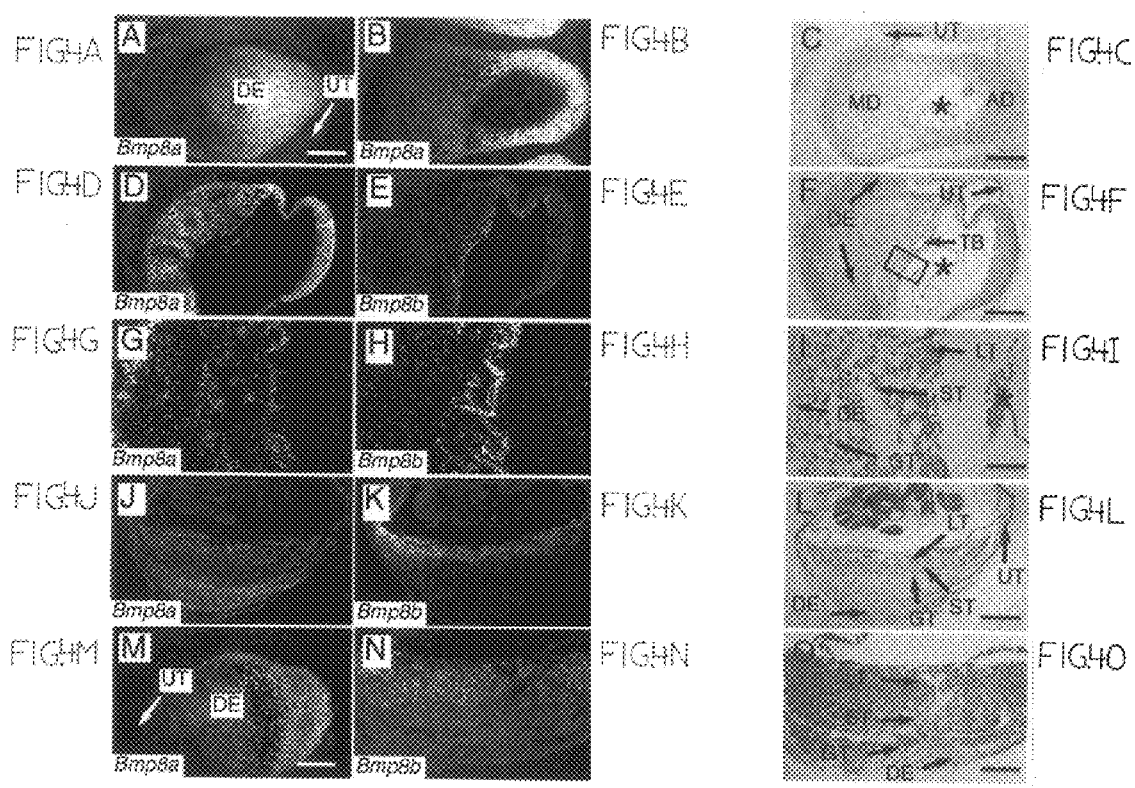

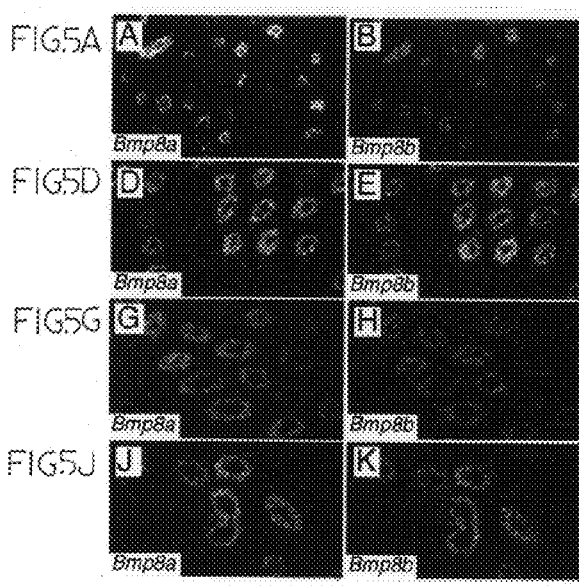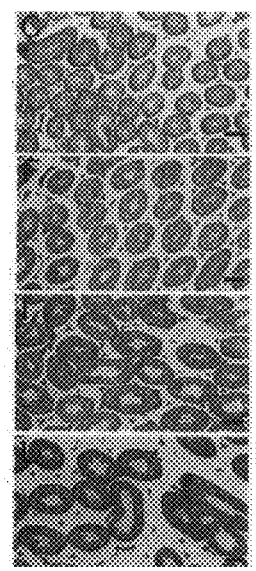

FIG.5M  FIG.5N  FIG.5O
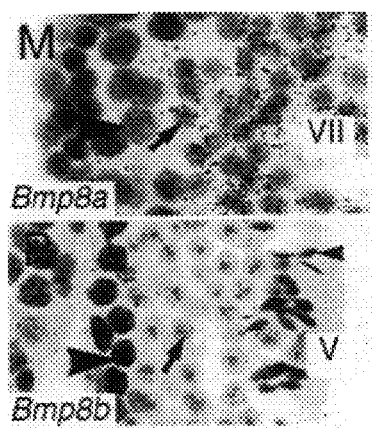
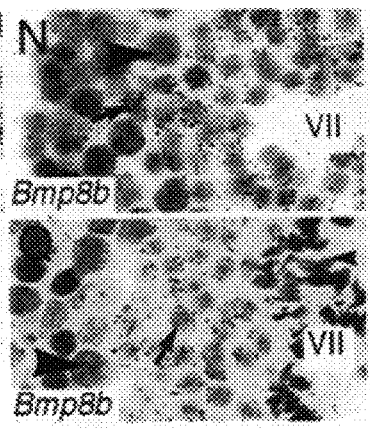
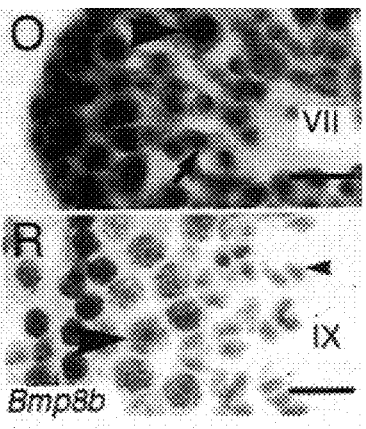
FIG.5P  FIG.5Q  FIG.5R

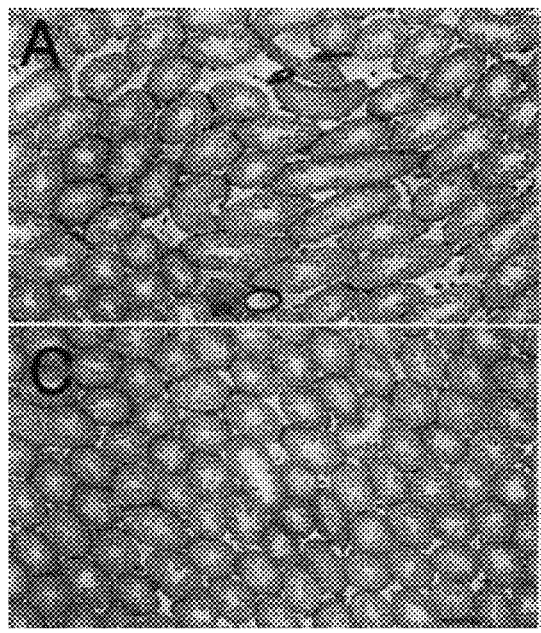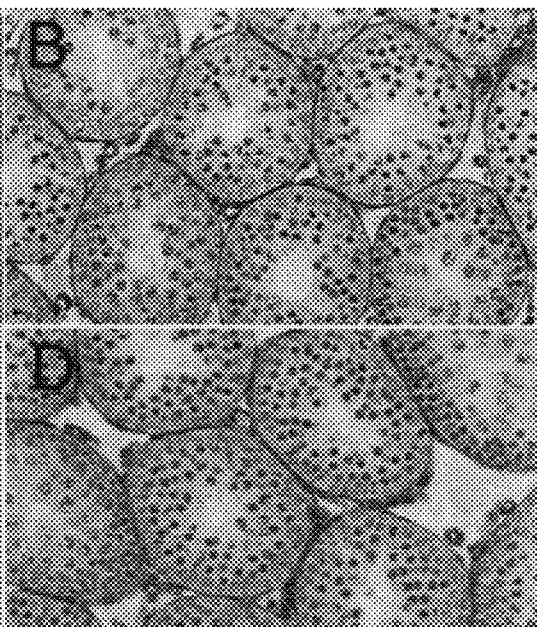
FIG.8A  FIG.8B
FIG.8C  FIG.8D

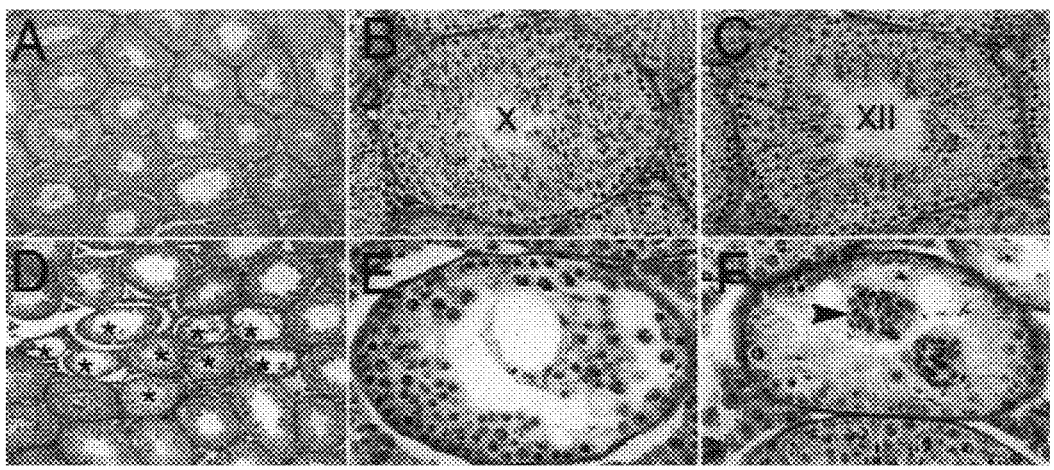
FIG.10A  FIG.10B  FIG.10C
FIG.10D  FIG.10E  FIG.10F
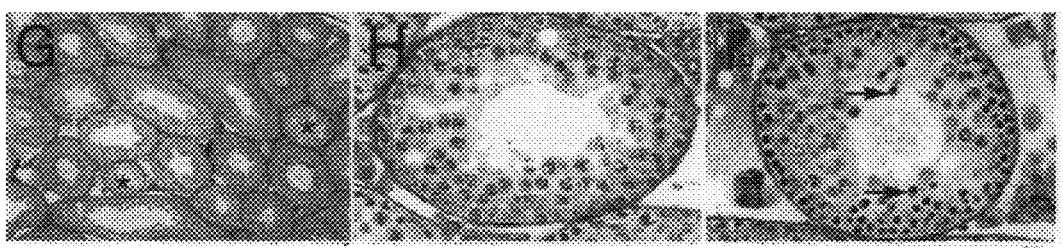
FIG.10G  FIG.10H  FIG.10I

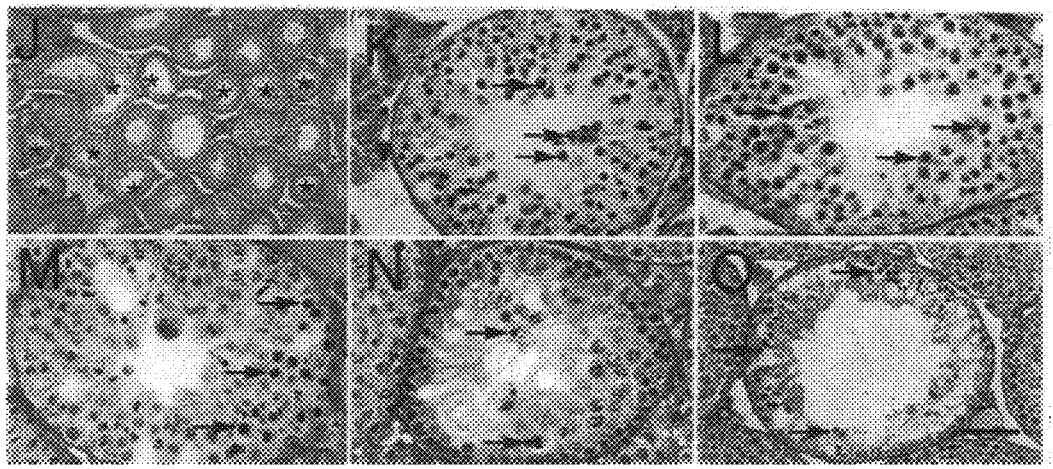

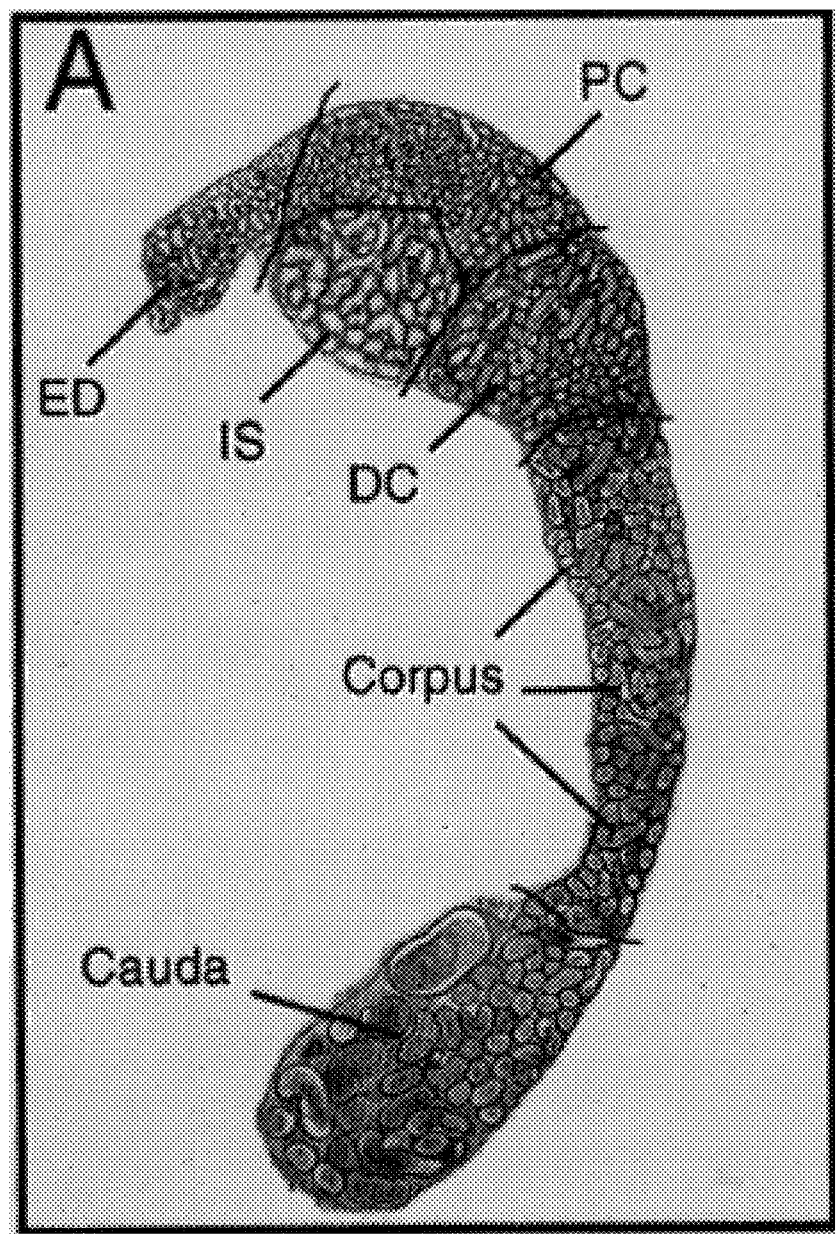
FIG. IIA

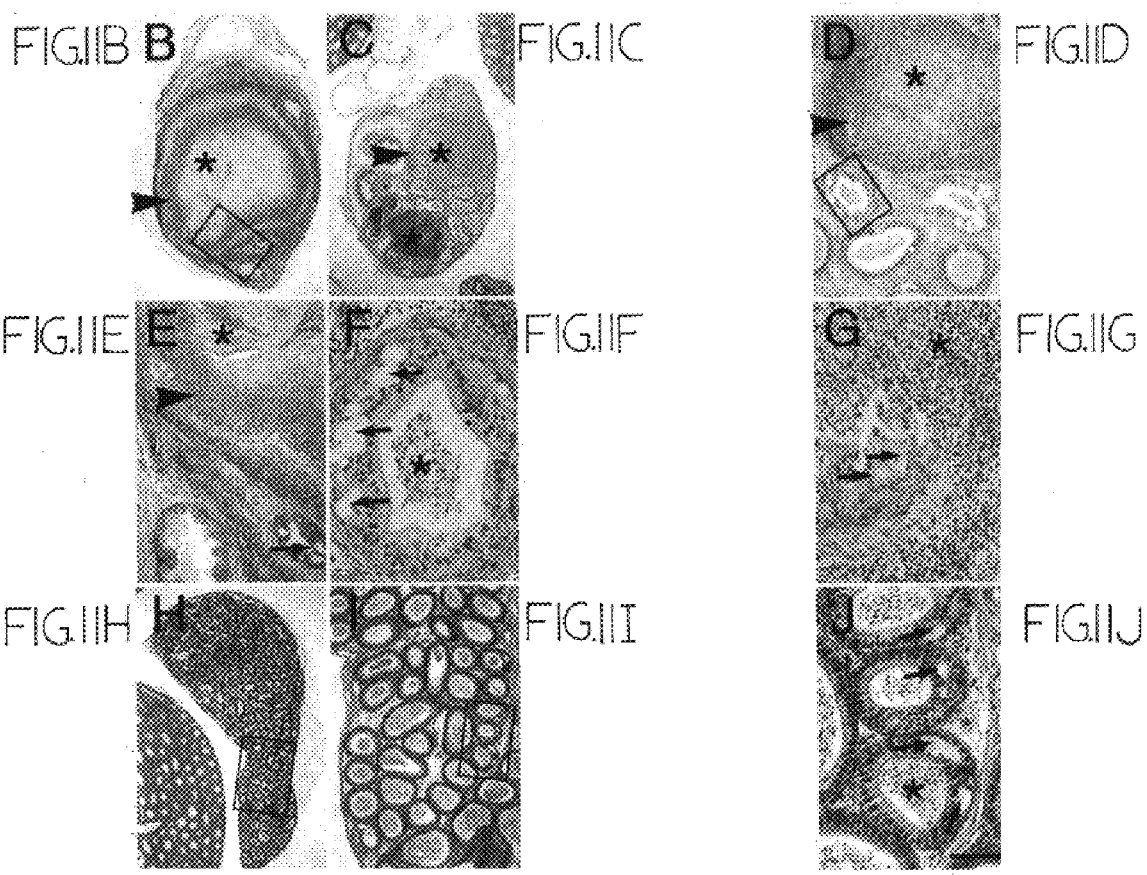

```
GCCAGGCACAGGTGCGCCGTCTGGTCCTCCCCGTCTCTGGCGTCAGCCCGAGCCCGACCAGCAGCTACCAGTGGATGCGCCGCGGCTGA
AAGTCCGAGATGGCTATGCTTCCCGGGCCACTCTGGCTATTGGGCCTTGCTCTGTGCCGCGTGGAGGCGGCCACGGTCCGCG
TCCCCGCACACCTGTCCCCAGCGTCGCCTGGGAGCGCGCGGAGCGCAGCGTGAAATCCTGGCGGTGCTCGGGC
TACCGGACGGCCCCGACCCCGTGCACAACCCGCCAGCGCCGGCGCTGCCCGGCGTCCGCGCCCCTCTTCATGTTGACCTATAC
CACGCCATGACCGATGACGACGGCGGGCCACCACAGGCTCACTTAGGCCGTGCCGACCTGGTCATGAGCTTCGTCAACAT
GGTGGAAACGCGACCCTGGGCTACCCTGGAGTTCCGGATCTACAAAGAACCCACCCCGCTCAACACAACCCTCCACATCAGCATGTTC
AGGCTGTCACAGCTGCTGAGTTCCGGATCTACAAAGAACCCACCCCGCTCAACACAACCCTCCACATCAGCATGTTC
GAAGTGGTCCAAGAGCACTCACAGCAGCCAGTCTGACTTGTTCTTTTTGGATCTTCAGACGCTCGGGACTCGGGACGAGGCTG
GCTGGTGCTGGACATCACAGCAGCCAGTGACCGATGGCTGCTGTCTGCTGGGCCAGCGATCATCACAAGGACCTGGGACTCCGCTCTATGTGAAA
CCGCGGATGGGCACACATGGATCCTGGCCTGGCTGGGGCCCCTCGGGCAGCAGCATGCCAGCCCCTCTATGTGTA
ACCTTCTTCAGGGCCAGCCAGAGTCCTGTGCGCGGGATCTTTGATGATGGCCACGGTTCCCGCGGCAGAGAGGTTGCCGCAGGCATG
CGAGCTTCCGCACCCCAACAAACTCCCAGGGATCTTTGATGATGGCCACGGTTCCCGCGGCAGAGAGGTTGCCGCAGGCATG
AGCTCTACGTCAGCTTCCGTCGACTCCTGTATGAACGCCACCAACATGCCACCTCTTGCAGTTGCACCTGATGAAGCCAGA
GAGTGTGCTTTCCCCAAGGCATGCTGTGCACCCACCAAACTGAGTGCCACCTCTGTGCTGTACTATGACAGCAGCAACAATGTCATCC
TGTTGTCCCCAAGGCATGCTAACATGTGGTCAAGGCCTGTGGCCACCTCTGTGCTGTACTATGACAGCAGCAACAATGTCATCC
TGCGTAAACACCGTAACATGTGGTCAAGGCAGAAACCCTTCGTTATCATAGCTCAGAGCAGCATGGGAGGCCCCTTCACTTCC
TCTGGCCGGCCCCTCCTGCTAAAATTCGGTCTTTCCCAGTTCCTGTCTTCCCTTCATGGGGTTTCGGGGCTATCACCCCGCCCCCTC
CCTGGCCACTTCCTACCCCAAGCATAGACTGATCCTTGGCCATCCTCAGCCACCTCCTCAGCACACCAAGCTAACTGGATGGTCTAAGAAGCCCTGAATTCTA
CATCCTCCACATGAGGAAGACTGATCCTTGGCCATCCTCAGCCACCTCCTCAGCACACCAAGCTAACTGGATGGTCTAAGAAGCCCTGAATTCTA
GCCCACATGAGGAAGACTGATCCTTGGCCATCCTCAGCCACCTCCTCAGCACACCAAGCTAACTGGATGGTCTAAGAAGCCCTGAATTCTA
AACTAGATGATCTGGCTCTCTGCCACCATTCATTGTGCAGTTGGGACATTTTAGGTATAACAGACACATACACTTAGATCA
ATGCATCGCTGTACTCCTTGAAATCAGAGACAGGAGAATCTCTGTGAGTTCAAGGCCACATAGAGAAAGAGCCTGTCTCGGGAGCAGAGAAAAAA
CCAGGCTAAAGAGAGACAGGAGAATCTCTGTGAGTTCAAGGCCACATAGAGAAAGAGCCTGTCTCGGGAGCAGAGAAAAAA
AAAAAAAA
```

FIG. 13

MAMRPGPLWLLGLALCALGGGHGPRPPHTCPQRRLGARERRDMQREILAVLGLPGRPRPRAQPAAARQPASAPLFMLDLY

HAMTDDDDGGPPQAHLGRADLVMSFVNMVERDRTLGYQEPHWKEFHFDLTQIPAGEAVTAAEFRIYKEPSTHPLNTTLHI

SMFEVVQEHSNRESDLFFLDLQTLRSGDEGWLVLDITAASDRWLLNHHKDLGLRLYVETADGHSMDPGLAGLLGRQAPRS

RQPFMVTFFRASQSPVRAPRAARPLKRRQPKKTNELPHPNKLPGIFDDGHGSRGREVCRRHELYVSFRDLGWLDWVIAPQ

GYSAYYCEGECAFPLDSCMNATNHAILQSLVHLMKPDVVPKACCAPTKLSATSVLYDSSNNVILRKHRNMVVKACGCH

FIG. 14

ACACTCGCTATTCCCTACCGCGCGGGGCCCAGCGTTGCTCTCGCGGGACCTACAGGCTGGCTCTGCCTGCGGACGGCGGTGGAGCAGTCGTCTTAGAG
CTGCCCGGCGACAGTGCGAACTCGGGATCCGGGCGCTGTCCCATCCTTGTCGTCGGAGGCGTCGGATGCGAGTCCGCTAAAGTCCGAGAT
GGCTGCGCGTCCGGACTCCTATGGCTACTGGGCCTGGCCTGCTGTGCGTGTTGGGCGCGGTCACCTCTCCGCATCCCCGCACGTCTTTCCCCAG
CGTCGACTAGGAGTACGGCGAGCCCCGCGACATGCAGCCGCGAGATTCGGGAGGTGCTGGGGCGGCCCCCGATCCGAGCACCGGTCG
GGGCTGCCCAGCAGCCAGCGTCTCGCCGCCTCTTTATGTTGACCTGTACCGTGCCATGACGATGACAGTGGCGGTGACCCCGCAGCCTCA
CTTGACCGTGCTGACCTGATTATGAGCTTTGTCAACATAGTGGAACGCGACCCTGGGCTACCAGGAGCCACACTGGAAGGAATTCCAC
TTTGACCTAACCCAGATCCCTGCTGGGAGGCTGTCACAGCTGCTGAGTTCCGAGTTCCGGATCTACAAAGAACCCAGTACCACCCGCTCAACACAACCT
TCCACATCAGCATGTTCGAAGTGGTCCAAGAGCACTCCAACAGGGAGTCTGACTTGTCCTTTTGATCTTCAGACGCTCCGATCTGGGACGA
GGGCTGGCTGGTGCTGGACATCAGCAGCCAGTGACCGATGGCTGCTGGAACAGCACCAGCTAGGACTCCGCCTCTATGTGGAAACCGAG
GATGCCACGGCATAGATCCTGGCCTGGCTGGTCGCTGCTTGGAGACAAGCAGCTAATCAACCAGCTGCCGCACTCCAACAAACACCT
ACCAGAGTCCTGTGCGGGCCCCTCGAACAGCAAGACCACTGAAGAAGCAGTCAGTGAGCTCTATGTCAGCTTCGTGCTTGGCTGGAC
AGGAATCCTTGATGATGGCCACGGTTCTCACGGCAGAGAAGTTTGCCGCACAGGGAGGAGTCATCTACCACTGAACTCCACCAACCACCCA
TCTGTCATTGCCCCCAGGCTACTCCGCCTATTACGTGCTGGGAGGTGCATCATCCCCAAGGTGTGCTGCCTACTGAGCTGAGTGCCATTTCTCGCTCTA
CTATGCAGGCCCTGGTACATCTGATGAAGCCAGATATCATCCGCCAACATGGTAGTCCAGCCTAGTCAGCCCTGCCCAACAGCCTGCTGCC
TGATAGAAACAATAATGTCATCCTGCGCAGGAGCCAACATGGTAGTCCAGCCTAGTCAGCCTGTGCCACTGAGTCCCGCCAACAGCCTGCTGCC
ATCCCATCTATCTAGTCAGGCTCTTGCCAAGGCAGGAAACAAGAGGGAAGGCAGTGCTTTCAACTCCATGTCCACATTTACAGTCTT
GGCCCTCTCTGTTCTTTTGCCAAGGCTGAGAGATGTCCTAGTTATAACCCTGTGACCTCAGTAGCCCATCTCTCATCTCCCCAAACTCCCC
CAATGCAGCCAGGGCATCTATGTCCTTTGGGATTGCCACAGAAGTCCAATTACCAACTTATTCATGATCACTACTGCCCAGCCTGACTTGAA
CCTGAACACAGGGCTAGAGCTCTTCAGGCTCTTCAGTATCCATCAGAAGATTTAGGTGTGCAGACATGGAAAGCTAGTAGTATCTCTCTCCATAGC
CTGTCTCTTGGGGGTGCAAAATGGGATTTCTAGAGAAGAGTTTAAAATATATGGAAAAGCTAGTAGTATCTCTCTCTCATCTAGCACT
TGGAAGCTGAGGCAGTTCAAGCCAGCTGGATATATCTAGATCTCATTCATATCTCATATCTCATCTCATCTCATCTATCTAT
CTATCTATCTATCTATCTATCCAGGCTCTATATATATATATCAAGATCTTCCTTCAAAACAAACAAAACCTGTGTATTTAGGATCTCAG
TCACTAAACCTCTGCCACAAGAGGCCAGCAGGCCACAAGAGGCTAATGAAAAAACCTATTGCGGATTATCATCTGGATTTAGGCATCGTCATTAAAG
AAAATGCCAACAGTTTCCCTG

FIG. 15

MAARPGLIWLLGLALCVLGGGHLSHPPHVFPQRRLGVREPRDMQREIREVLGLPGRPRSRAPVGAAQQPASAPLFMLDLY

RAMTDDSGGTPQPHLDRADLIMSFVNIVERDRTLGYQEPHWKEFHFDLTQIPAGEAVTAAEFRIYKEPSTHPLNTTFHI

SMFEVVQEHSNRESDLSFLDLQTLRSGDEGWLVLDITAASDRWLLNHHKDLGLRLYVETEDGHGIDPGLAGLLGRQAPRS

RQPFMVGFFRANQSPVRAPRTARPLKKQLNQINQLPHSNKHLGILDDGHGSHGREVCRTGELYVSFRDLGWLDSVIAPQ

GYSAYYCAGECIYPLNSCMNSTNHATMQALVHLMKPDIIPKVCCVPTELSAISLLYDRNNNVILRRERNMVVQACGCH

COMPOSITIONS AND METHODS OF MAKING EMBRYONIC STEM CELLS

This Application claims the benefit of U.S. Provisional applications 60/012,386 Filed Feb. 28, 1996 and 60/012,384 filed Feb. 28, 1996.

GOVERNMENT SUPPORT

This invention was supported in part by a grant from the U.S. Government (NIH Grant No. CA 48799) and the U.S. Government may therefore have certain rights in the invention.

FIELD OF THE INVENTION

The field of the invention is human and nonhuman mammalian spermatogenesis.

BACKGROUND OF THE INVENTION

The bone morphogenetic proteins (BMPs) are members of a large, highly conserved, family of extracellular polypeptide signaling molecules related to transforming growth factor-$\beta$ (TGF-$\beta$). There is now considerable evidence from expression studies, and from the in vivo effects of misexpression and mutations, that Bmp genes play key roles at many different stages of embryonic development, in both invertebrates and vertebrates (Kingsley et al., 1994, Dev. Biol. 166:112–122; Massague et al., 1994, Trends Cell Biol. 4:172–178; Hogan, 1995, Sem. Dev. Biol. 6:257–265). In the mouse, both spontaneous and induced mutations in a number of Bmp genes have shed light on their function in vivo. The first example to be described was a series of short ear mutations, which result from alterations in the Bmp5 gene (Green, 1968, J. Exp. Zool. 167:129–150; Kingsley et al., 1992, Cell 71:399–410; King et al., 1994, Dev. Biol. 166:112–122). Null mutants are viable, but have defects in cartilage development in specific parts of the skeletal system, as well as abnormalities in the lung, kidney and ureter in some genetic backgrounds.

Mutations in other Bmp genes have been generated by homologous recombination in embryonic stem cells. For example, Bmp7 homozygous null mutant mice die shortly after birth with major defects in eye, kidney and limb development (Dudley et al., 1995, Genes Dev. 9:2795–2807; Luo et al., 1995, Genes Dev. 9:2808–2820). Most Bmp4 homozygous mutant embryos die around the time of gastrulation and many exhibit a deficiency in extraembryonic and posterior/ventral mesoderm (Winnier et al., 1995, Genes Dev. 9:2105–2116), a finding consistent with the effect of BMP4 on mesoderm patterning in Xenopus embryos (Jones et al., 1992, Development 115:639–647; Graff et al., 1994, Cell 79:169–179; Harland, 1994, Proc. Natl. Acad. Sci. USA 91:10243–10246). Mutations have also been described in other members of the BMP superfamily, including mouse nodal, and Gdf5 (brachypodism) (Zhou et al., 1993, Nature 361:543–547; Conlon et al., 1994, Development 120:1919–1928; Storm et al., 1994, Nature 368:639–643).

Spermatogenesis takes places within the confines of the seminiferous tubules in the testis. A typical tubule is ensheathed by an outer basal lamina. Inside the lamina and attached to it is a layer of spermatogonial cells which continue to divide very slowly from puberty to late adult life. The self-renewing spermatogonial stem cell (known as an $A_O/A_S$ cell) is very rare and it gives rise to other less primitive spermatogonial cells. These give rise to nondividing spermatocytes which leave the basal layer and move towards the center of the tubule. These spermatocytes undergo meiosis and eventually give rise to mature sperm. The spermatogonia and differentiated derivatives are in intimate contact with the somatic Sertoli cells. Little is known about the growth factors/cytokines which regulate the proliferation of the spermatogonial stem cells, their differentiation into spermatocytes, the entry of the spermatocytes into meiosis, their differentiation into sperm and the way in which this whole complex process is co-ordinated in vivo. It has been difficult to obtain populations of cells having high concentrations of the most primitive spermatogonial stem cells in part because they form a very small proportion of the total spermatogenic cells of the testis. Additionally, cultures of spermatogonia generally only remain viable for short periods of time, that is, about 24–48 hours.

SUMMARY OF THE INVENTION

The invention relates to a method of proliferating mammalian spermatogonial stem cells, comprising culturing spermatogonial stem cells in the presence of BMP8, or a biologically active fragment or an agonist thereof, to effect proliferation of the cells.

Also included in the invention is a method of differentiating mammalian spermatogonial stem cells, comprising culturing spermatogonial stem cells in the presence of BMP, or a biologically active fragment or an agonist thereof, to effect differentiation of the cells.

In addition, the invention relates to a method of extending viability of a mammalian spermatogonial cell population, comprising culturing the spermatogonial cell population in the presence of BMP8, or a biologically active fragment or an agonist thereof, thereby extending the viability of the cultured spermatogonial cell population.

In another aspect of the invention, there is provided a method of inducing apoptosis of spermatocytes in culture comprising incubating the spermatocytes in the substantial absence of BMP8, or a biologically active fragment or an agonist thereof, thereby inducing apoptosis of spermatocytes.

Also included in the invention is a method of inhibiting proliferation of spermatogonial stem cells in culture, comprising incubating a population of spermatogenic cells in the substantial absence of BMP8 to effect inhibition of proliferation of the cells.

Further provided is a method of effecting the proliferation of mammalian spermatogonial stem cells in vivo in a mammal, comprising administering to the mammal BMP8, or a biologically active fragment or an agonist thereof, suspended in a pharmaceutically acceptable carrier, to effect proliferation of the cells in the mammal.

The invention also includes a method of effecting differentiation of mammalian spermatogonial stem cells in vivo in a mammal, comprising administering to the mammal BMP8, or a biologically active fragment or an agonist thereof, suspended in a pharmaceutically acceptable carrier, to effect differentiation of the cells in the mammal.

A method of extending viability of a mammalian spermatogonial cell population in vivo in a mammal is also provided. The method comprises administering to the mammal BMP8, or a biologically active fragment or an agonist thereof, suspended in a pharmaceutically acceptable carrier, thereby extending the viability of the mammalian spermatogonial cell population in the mammal.

The invention also relates to a method of inducing apoptosis of spermatocytes in vivo in a mammal comprising administering to the mammal BMP8, or a biologically active fragment or an agonist thereof, suspended in a pharmaceutically acceptable carrier, thereby inducing apoptosis of spermatocytes in the mammal.

A method of inhibiting proliferation of spermatogonial stem cells in vivo in a mammal is further provided. The method comprises administering to the mammal an antagonist of BMP8 suspended in a pharmaceutically acceptable carrier, to effect inhibition of proliferation of the cells in the mammal.

In yet another aspect, the invention includes a method of selectively obtaining a proliferating population of spermatogonial stem cells in culture, comprising adding BMP8 to the population of cells, thereby selectively obtaining a proliferating population of spermatogonial stem cells.

There is also included a method of treating infertility in a male mammal, comprising administering to the mammal BMP8, or a biologically active fragment or an agonist thereof, suspended in a pharmaceutically acceptable carrier.

Ina preferred embodiment, the BMP8 is administered to the testes of the mammal.

The invention includes a mammalian male contraceptive comprising a BMP8 antagonist.

The invention also includes a method of identifying an antagonist of BMP8, comprising adding a test compound to a culture of spermatogonial cells in the presence or absence of BMP8 and measuring the level of proliferation or differentiation of the cells, wherein a lower level of proliferation or differentiation of the cells in the presence of the test compound, compared with the level of proliferation or differentiation of the cells in the absence of the test compound, is an indication that the test compound is a BMP8 antagonist.

Further included is a method of identifying an agonist of BMP8, comprising adding a test compound to a culture of spermatogonial cells in the presence or absence of BMP8 and measuring the level of proliferation or differentiation of the cells, wherein a higher level of proliferation or differentiation of the cells in the presence of the test compound, compared with the level of proliferation or differentiation of the cells in the absence of the test compound, is an indication that the test compound is a BMP8 agonist.

In addition, the invention relates to a method of stimulating hair growth in a mammal, comprising administering a hair growth stimulating amount of BMP8 to the hair follicles of the mammal.

A method of isolating a BMP8 receptor on a cell is also provided. The method comprises binding BMP8 to a BMP8-responsive population of cells, and isolating the protein on the cells to which the BMP8 binds.

The invention features a purified population of spermatogonial stem cells.

The invention also features a method of making a population of mammalian pluripotent embryonic stem cell, comprising incubating a population of spermatogenic cells in a composition comprising a growth enhancing amount of basic fibroblast growth factor, leukemia inhibitory factor, membrane associated steel factor, and soluble steel factor, thereby making a population of pluripotential embryonic stem cells.

A population of pluripotential embryonic stem cells produced by the just described method is also included.

In addition a composition comprising BMP8, a fibroblast growth factor, leukemia inhibitory factor, membrane associated steel factor, and soluble steel factor in amounts to enhance the growth of and allow the continued proliferation of germ cells and the formation of pluripotent embryonic stem cells from the germ cells is included.

BRIEF DESCRIPTION OF THE DRAWINGS

FIG. 1 is a diagram depicting a comparison of the deduced amino acid sequences of murine BMP8A/OP2 (upper sequence) and BMP8B (lower sequence) [SEQ ID NOS:2 and 4]. Identical residues are aligned with a dash, similar residues are aligned with a colon.

FIG. 2, comprising FIGS. 2A and 2B, is a diagram depicting the chromosomal location of Bmp8a and Bmp8b. These two genes were mapped using the Jackson Laboratory interspecific backcross panel mice (C57BL/6JEi x SPRET/Ei) F1 x SPRET/Ei (Rowe et al., 1994, Mamm. Genome 5:253–274). In the case of both genes, 94 of the (C57BL/6JEi x SPRET) F1 x SPRET/Ei backcross progeny were typed for inheritance of the *M. domesticus* or *M. spretus* alleles.

FIG. 2A is a partial chromosome 4 linkage map showing, on the right hand side, the location of the two genes in relation to surrounding loci mapped in the backcross and, on the left hand side, the position of surrounding genes taken from the composite map in the Mouse Genome Database.

FIG. 2B is a haplotype map. The stippled boxes indicate inheritance of an *M. domesticus* allele while the unfilled boxes indicate inheritance of an *M.spretus* allele. R is the recombination distances in centimorgans, SE is the standard error.

FIG. 4, comprising FIGS. 4A–4O, is a series of images depicting localization of Bmp8 transcripts in uterus and placenta by in situ hybridization. FIGS. 4A, 4B, 4D, 4E, 4G, 4H, 4J, 4K, 4M, and 4N are dark-field photomicrographs and FIGS. 4C, 4F, 4I, 4L and 4O are bright-field photomicrographs. Scale bar is 200 μm for FIGS. 4G–4I and 800 μm for FIGS. 4A–4F and 4J–4O.

FIG. 4A is a section through a 7.5 d.p.c. implantation site depicting high levels of Bmp8a transcripts in the antimesometrial decidual cells (DE), but not in the surrounding myometrium of the uterus (UT).

FIG. 4B and FIG. 4C is a section through 8.5 d.p.c. uterus, deciduum, and embryo showing high levels of Bmp8a transcripts in the antimesometrial decidual cells (AD) and lower levels of hybridization signals in the mesometrial decidual cells (MD). No hybridization signals are observed in the myometrium and embryo proper (*).

FIGS. 4D, 4E and 4F are sections through 9.5 d.p.c. uterus, placenta, and embryonic membranes depicting high levels of Bmp8a transcripts in the deciduum and both Bmp8a and Bmp8b transcripts in trophoblast cells (TB), but not in the myometrium of uterus or extraembryonic membranes (*).

FIGS. 4G, 4H and 4I depict high power magnification of the region boxed in FIG. 4F showing Bmp8a transcripts in the deciduum, spongiotrophoblast cells (ST), and labyrinthine region of the placenta (LT), but not in the giant trophoblasts (GT) and extraembryonic membranes. Bmp8b transcripts are predominantly localized in the labyrinthine region of the placenta.

FIGS. 4J, 4K and 4L are sections through 10.5 d.p.c. uterus, placenta, and embryo showing decreased levels of Bmp8a transcripts in the antimesometrial deciduum and increased levels of hybridization in the mesometrial deciduum. Both Bmp8a and Bmp8b transcripts are detected in the labyrinthine region of the placenta. Neither Bmp8a nor Bmp8b transcripts are detected in the embryo proper nor in the myometrium of uterus.

FIG. 4M is a section through uterus and deciduoma depicting Bmp8a transcripts in the decidual cells, but not in the myometrium.

FIGS. 4N and 4O is a section through 13.5 d.p.c. placenta showing Bmp8b transcripts in the labyrinthine trophoblasts, but not in the spongiotrophoblasts, giant trophoblasts or the decidual cells.

FIG. 5, comprising FIGS. 5A–5R, is a series of images depicting localization of Bmp8 transcripts in the testes by in situ hybridization. Sections of testes from animals at 3.5 weeks (mid puberty; FIGS. 5A, 5B, and 5C), 5 weeks (later puberty; FIGS. 5D, 5E, and 5F), 7 weeks (young adult;FIGS. 5G, 5H, and 5I), and 12 weeks (adult;FIGS. 5J, 5K, and 5L) were used for in situ hybridization and histology. FIGS. 5A, 5B, 5D, 5E, 5G, 5H, 5J, and 5K depict adjacent sections of testes at different ages hybridized with riboprobes for Bmp8a and Bmp8b as indicated on the figure. FIGS. 5C, 5F, 5I, and 5L depict sections stained with periodic acid Schiff's (PAS) reagent and hematoxylin for accurate staging of seminiferous tubules. Bmp8a and Bmp8b transcripts are localized to stage VI–VIII seminiferous tubules in a similar pattern in animals at the different ages shown. FIGS. 5M, 5N, and 5O are adjacent sections from a 3.5 week testis. FIGS. 5M and 5N depict the fact that the transcripts of both genes are predominantly localized to the round spermatids (arrows) and low levels of signals are present in some pachytene spermatocytes (large arrow head). FIG. 5O is stained with PAS and hematoxylin showing a stage VII seminiferous tubule as judged by the morphology of acrosomes of the round spermatids (arrow). FIGS. 5P, 5Q, and 5R are sections from a 7 week testis hybridized with Bmp8b riboprobe. Hybridization signals are observed in the round spermatids (arrow) of stage VII seminiferous tubule in FIG. 5Q, but not in the round spermatids of stage V or stage IX seminiferous tubules. No detectable signals are observed in the elongated spermatids (small arrow heads). Sections in FIGS. 5P, 5Q, and 5R were exposed for 5 days, and all other sections were exposed for 14 days. The scale bar is 100 μm for FIGS. 5A–5L and 25 μm for FIGS. 5M–5R.

FIG. 6 comprising

FIG. 6A is a schematic representation of the Bmp8a wild-type allele on the top, targeting construct in the middle, and the recombinant Bmp8a$^{tm1blh}$ allele at the bottom. Genomic DNA fragments used as the short (5') and long (3') homology arms of the targeting vector are indicated as thick solid lines. Coding exons 2, 3, 4, 5, 6, and the first half of exon 7 (Ozkaynak et al., 1992, J. Biol. Chem. 267:25220–25227) are indicated as darkly-stippled boxes (E2–E7). The second half of exon 7 containing the 3' untranslated region is indicated as an open box. Expression cassettes PGK-TKA+, PGK-neo$^r$ (Rudnicki et al., 1992, Cell 71:383–390), and MC1DT-A (Yagi et al., 1990, Proc. Natl. Acad. Sci. USA 87:9918–9922) are also shown as boxes with arrows underneath showing direction of transcription. Restriction enzyme abbreviations: (B) BamHI; (E) EcoRI; (S) SalI; (X) XbaI; (Xh) XhoI.

FIG. 6B is an image of a genomic Southern blot hybridized to a cDNA probe derived from exons 2 and 3 of Bmp8a which is almost identical in sequence to exons 2 and 3 of Bmp8b. Therefore, EcoRI digested DNA reveals a 9 kb fragment for the wild-type Bmp8a locus and an 8 kb fragment for the wild-type Bmp8b locus. The 9 kb Bmp8a allele is reduced to 5 kb in the Bmp8$^{tm1blh}$ allele.

FIG. 6C is a genomic Southern blot hybridized to a cDNA fragment containing exons 4, 5, 6, and 7 as a probe. This probe is specific for Bmp8a and reveals two EcoRI fragments of 2.3 kb (containing exons 4, 5, and 6) and 2.0 kb (containing part of exon 7) for the wild-type allele and only a 2.0 kb fragment for the mutant allele.

FIG. 8 comprising FIGS. 8A–8H, is a series of images depicting a histological comparison of testes from 2 week-old animals of wild-type (+/+); FIGS. 8A and 8B, Bmp8a −/−(FIGS. 8C and 8D), Bmp8b −/−(FIGS. 8E and 8F), and Bmp8 compound heterozygous (FIGS. 8G and 8H) genotype. FIGS. 8A, 8C, 8E, and 8G are 10× power and FIGS. 8B, 8D, 8F, and 8H are 40× power. A typical representative histology from each genotype is shown. At this age, the testes of Bmp8b homozygous mutants are significantly smaller than the others and, in severe cases, only one layer of epithelium is present in the seminiferous tubule (FIGS. 8E and 8F; Zhao et al., 1996, Genes and Dev. 10:1657–1669). In contrast, in wild-type animals, Bmp8a homozygous mutant and compound heterozygous mutant testes, multiple layers of germ cells are present in the seminiferous epithelium. Bar is 200 μm in FIGS. 8A, 8C, 8E, and 8G and 50 μm in FIGS. 8B, 8D, 8F, and 8H.

FIG. 9, comprising FIGS. 9A, 9C, and 9E are 5× power and FIGS. 9B, 9D, and 9F are 20× power. FIGS. 9A and 9B are sections of a wild type testis (17 weeks of age) showing normal spermatogenesis in all seminiferous tubules (the various stages of each tubule are indicated by roman numerals; Russell et al., 1990, In: Histological and histopathological evaluation of the testis, Eds. Russell et al., pp. 119–161, Cache River Press, Clearwater, Fla.). FIGS. 9C and 9D are sections of a homozygous Bmp8a mutant testis (22 weeks of age) with the most advanced germ cell degeneration observed. In this testis, very few spermatids were observed in the seminiferous tubules, while meiotic germ cells were found in most seminiferous tubules. However, a small number of tubules did lack most germ cells and even some of the Sertoli cells had disappeared, indicated by the *. Apoptotic germ cells exhibiting darkly-stained condensed nuclei were observed in most seminiferous tubules (arrows). FIGS. 9E and 9F are sections of a homozygous Bmp8b mutant testis (22 weeks of age) showing that all seminiferous tubules lack spermatogenesis and only Sertoli cells were left in a majority of the seminiferous tubules, indicated by the *. Some darkly stained cells (arrowhead) were observed in the center of some seminiferous tubules. These cells did not express Sertoli cell markers such Dhh and Cp-2 (Bitgood et al., 1996, Curr, Biol. 6:298–304; Wright et al., 1986, Biol. Reprod. 35:761–772; Wright et al., 1993, In: Cell and Molecular Biology of the Testis, Eds. Desjardins et al., pp.377–399, Oxford Univ. Press NY) and were most likely the spermatogonial germ cells which had detached from the basal lamina (Zhao et al., 1996, Genes and Dev. 10:1657–1669). Bar is 400µ in FIGS. 9A, 9C, and 9E and 100 µm in FIGS. 9B, 9D, and 9F.

FIG. 10, comprising FIGS. 10A–10O is a series of images depicting examples of milder forms of histological abnormalities observed in adult Bmp8a mutant testes. FIGS. 10A, 10B, and 10C are sections of a wild-type testis (22 weeks of age) showing normal spermatogenesis. FIG. 10A is at low power magnification; Panel B is a stage X seminiferous tubule at high power magnification; FIG. 10C is a stage XII seminiferous tubule at high power magnification; FIGS. 10D–10O are representative sections from testes of different Bmp8a homozygous null mutants (12–30 weeks of age). FIG. 10D, at low power magnification, shows germ cell degeneration in numerous seminiferous tubules, indicated by the *; FIGS. 10E and 10F are high power photomicrographs of seminiferous tubules similar to those indicated in FIG. 10D. No spermatids and only a few meiotic germ cells are present. Arrowhead indicates a cluster of darkly-stained cells in the center of the degenerated tubule which are similar to those observed in Bmp8b mutant testis as shown in FIG. 9F. FIG. 10G, at low power magnification, shows germ cell degeneration in two seminiferous tubules, indicated by the *. FIGS. 10H and 10I are high power photomicrographs of seminiferous tubules similar to those indicated in FIG. 10G. No spermatids are found in FIG. 10H and very few in are found in FIG. 10I. A few apoptotic spermatocytes with condensed and darkly-stained nuclei (small arrows) are present in FIG. 10I. FIG. 10J, at low power magnification, shows germ cell degeneration in a large proportion of the seminiferous tubules, indicated by the *. FIGS. 10K and 10L are two examples depicting the fact that germ cells are blocked in metaphase and degenerate. They have darkly stained chromatin and eosinophilic cytoplasm (arrows) and are positively stained by TUNEL labeling. FIG. 10M is a section of a seminiferous tubule containing 16 apparently apoptotic germ cells with condensed and darkly stained nuclei (arrows) in a small area of the tubule. Some of these cells are in close proximity to the basement membrane, suggesting that they are either dying spermatogonia or dying preleptotene spermatocytes. FIG. 10N is a section of a seminiferous tubule in which no spermatids are present and most meiotic germ cells have disappeared. However, the spermatogonia and preleptotene spermatocyte populations seem to be relatively normal. Arrows indicate apoptotic cells. FIG. 10O is a section of a seminiferous tubule showing most meiotic germ cells have degenerated. The remaining primary spermatocytes have condensed darkly stained nuclei (arrows). The presence of many elongated spermatids suggests that the previous round of meiosis was relatively unaffected. Bar is 200 µm in FIGS. 10A, 10D, 10G, and 10J, 50 µm in FIGS. 10B, 10C, and 10O, and 30 µm in FIGS. 10E, 10F, 10H, 10I, and 10K–10N.

FIG. 11, comprising FIGS. 11A–11J, is a series of images depicting histological abnormalities of epididymides of homozygous Bmp8a mutants and a compound Bmp8a/Bmp8b heterozygote. FIG. 11A depicts the histology of wild type adult epididymis showing the efferent duct (ED), initial segment (IS), proximal caput (PC), distal caput (DC), corpus, and cauda regions. FIG. 11B is a section of the cauda epididymis of a Bmp8a homozygous mutant revealing advanced granuloma formation in which mature sperm (indicated by the *) are surrounded by infiltrating leukocytes (arrowhead). FIG. 11C is a section of the cauda epididymis of a Bmp8 compound heterozygote revealing two foci of granuloma formation outside the epididymis tubule, with sperm (indicated by the *) in the center and leukocyte infiltration (arrowhead) in the periphery. FIG. 11D is a section of the same cauda epididymis as in FIG. 11C depicting sperm (indicated by the *) surrounded by infiltrating leukocytes (arrowhead) and the degenerating epididymis tubules. FIG. 11E is a high power magnification of the boxed region in FIG. 11B showing sperm infiltrating leukocytes (arrowhead), and degenerating tubules (arrow). FIG. 11F is a high power magnification of the boxed region in FIG. 11D showing a degenerating epididymis tubule with sperm inside (indicated by a *). The epithelial layer of the tubule contains multiple vacuoles (arrows), suggesting cell degeneration. FIG. 11G is a high power magnification of a section of the same cauda epididymis as in FIG. 11C showing sperm (indicated by the *) in the neighborhood of an erupted epididymal tubule (arrows). FIG. 11H is a section through the caput epididymis and testis of a homozygous Bmp8a mutant. FIG. 11I is a higher power magnification of the boxed region in FIG. 11H showing the vacuolated epithelium in the tubules of the distal caput region. FIG. 11J is a high power magnification of the boxed region in FIG. 11I showing the vacuolated epithelium of the epididymis tubules (arrows). Bar is 800 µm in FIGS. 11A, 11B, 11C, and 11H; 200 µmin FIGS. 11D, 11E, and 11I; 50 µm in FIGS. 11F, 11G, and 11J.

FIG. 12, comprising FIG. 12A is a dark-field photomicrograph of a section through a wild-type testis and epididymis hybridized with antisense RNA probe directed against the 3' untranslated region of Bmp8a mRNA. Bmp8a is expressed in the stage 6–8 round spermatids, and therefore, shows stage-specific hybridization in the testis. Bmp8a transcripts are also detected in the initial segment of the caput epididymis, but at lower levels than in the testis. FIG. 12B is a bright-field photomicrograph of the same section as in FIG. 12A. FIG. 12C is a dark-field photomicrograph of a section through a wild-type testis and epididymis hybridized with an antisense RNA probe against the pro-region of Bmp7 mRNA. Bmp7 transcripts are detected in the initial segment of the caput epididymis at high levels. FIG. 12D is a corresponding brightfield photomicrograph of the same section as in FIG. 12C. IS, initial segment; PC, proximal caput; and DC, distal caput. Bar is 800 µm.

FIG. 13 is the nucleotide sequence of cDNA encoding BMP8A [SEQ ID NO:1].

FIG. 14 is the amino acid sequence of BMP8A [SEQ ID NO:2].

FIG. 15 is the nucleotide sequence of DNA encoding BMP8B [SEQ ID NO:3].

FIG. 16 is the amino acid sequence of BMP8B [SEQ ID NO:4].

DETAILED DESCRIPTION OF THE INVENTION

Figure 3A:
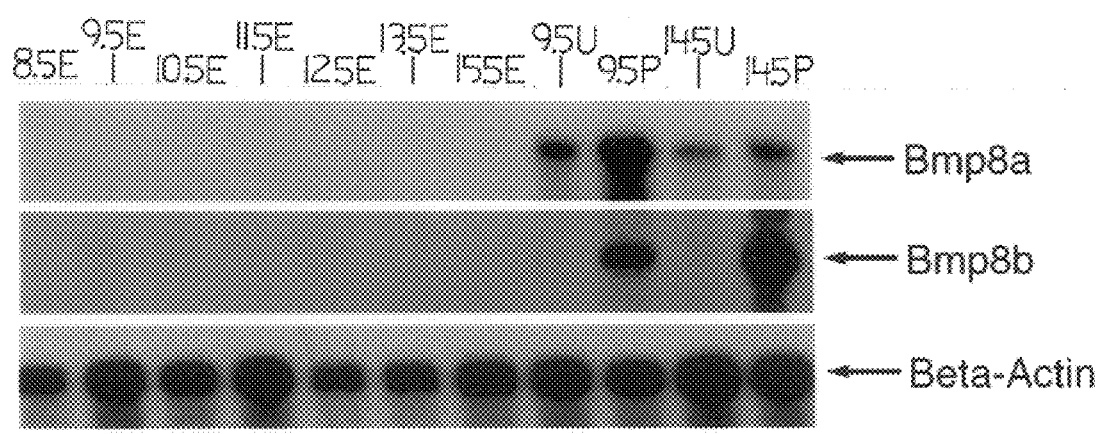
FIG. 3A is an image depicting detection of Bmp8a and Bmp8b RNAs in placenta and uterus using RNase protection assays. Ten micrograms of total RNA from 8.5–15.5 d.p.c. embryos and 9.5 and 14.5 d.p.c. placentae and uteri was used in each hybridization mixture comprising antisense riboprobes generated from Bmp8a UTR380 and Bmp8b BN260 (as shown in FIG. 3B). Bmp8a transcripts were detected in 9.5 d.p.c. and 14.5 d.p.c. placentae and uteri. Bmp8b transcripts were detected only in placentae but not in the uteri. Transcripts derived from either gene were not present at significant levels in the embryos assayed. β-actin was used as a control for the assessment of RNA levels in the experiments.

It has been discovered in the present invention that BMP8 is necessary for survival of spermatocytes and for the proliferation of spermatogonial cells. Thus, the invention provides a highly useful means of obtaining cultures of cells enriched for early stage, spermatogonial stem cells. Furthermore, the invention provides a means of treating infertility in males by supplying the BMP8 protein. Other uses and advantages of the invention are discussed further herein.

Although it appears that only a single BMP8 gene is present in humans, the data presented herein establishes the presence of two highly related and closely linked genes in the mouse which are designated herein as Bmp8a and Bmp8b. Previous studies using Northern blot analysis of poly(A)+RNA, had concluded that Bmp8a/Op2 is expressed in the 8.5 and 10.5 d.p.c. mouse embryo (Özkaynak et al., supra). However, as described herein, it was not possible to detect either Bmp8a or Bmp8b transcripts in the mouse embryo proper between 7.5 and 10.5 d.p.c. using a variety of different techniques such as RNAse protection, RT-PCR, cDNA library screening and in situ hybridization. In contrast, high levels of Bmp8 RNA were found in the placenta and decidual cells of the uterus around the embryo. In addition, it has been discovered in the present invention that both Bmp8a and Bmp8b are expressed in the germ cells of the testis at specific stages of spermatogenesis. Although three other members of the TGF-β gene family, for example, Müllerian inhibiting substance, activin, and inhibin, are expressed in the testis, transcripts specifying these genes are found predominantly in somatic Sertoli cells (Cate et al., 1990, In Sporn et al. Eds., Peptide Growth Factors and Their Receptor, Springer-Verlag, Berlin, Vol. 2, pp. 179–210); Steinberger et al., 1976, Endocrinology 99:918–921; Bicsak et al., 1987, Mol. Cell. Endocrinol. 49:211–217; Meunier et al., 1988, Proc. Natl. Acad. Sci. USA 85:247–251; Bhasin et al., 1989, Endocrinology 124:987–991).

Until the present invention, it was not known that Bmp8a and Bmp8b are expressed in the germ cells of the testis. The data presented herein therefore establish that BMP8A and BMP8B are required for mammalian spermatogenesis and maternal-fetal interactions and are not required for embryonic development as was heretofore believed.

As used in the specification and in the claims, "a" can mean one or more, depending upon the context in which it is used.

As used throughout this application, mammals can include, for example, rats, rabbits, guinea pigs, goats, pigs, cows, and humans.

The term "Bmp8" refers to nucleic acid encoding BMP8 protein. Bmp8 should be construed to refer to a DNA, a cDNA or an RNA encoding BMP8. The use of the term Bmp8 should also be construed to refer to both Bmp8a and Bmp8b, unless each of Bmp8a and Bmp8b is individually specified. Although the mouse Bmp8a and Bmp8b genes are exemplified herein, the use of the term "Bmp8" should also be construed to include homologs of mouse Bmp8, which homologs share homology with mouse Bmp8 genes. Thus, the invention should be construed to include Bmp8 genes from mice, and any other mammal, including rats, rabbits, guinea pigs, goats, cows, pigs and humans, etc.

Similarly, the use of the term "BMP8" should be construed to include any homolog of BMP8, e.g., mouse BMP8A and /or mouse BMP8B, human BMP8 (Genetics Institute, Cambridge, Mass.), or active portions either alone or in a larger polypeptide. These proteins are also referred to as OP-2 , OP-3 (Creative Biomolecules, Hopkinton, Mass.). The human OP-2 protein is homologous to mouse BMP8A and the human OP-3 protein is homologous (about 78% identical in amino acid sequence in the mature region of the protein) to the mouse BMP8B protein. Homologs of BMP8 include proteins which share homology with either of mouse BMP8A or BMP8B are described herein and which function in a manner similar to the mouse BMP8 proteins described herein. It is also contemplated that BMP8A and BMP8B can be used together. BMP8 can mean either BMP8A or BMP8B, particularly as it refers to human BMP8 proteins, unless each individual protein is so specified.

Thus, while nucleic acid encoding mouse BMP8A and BMP8B have been initially discovered, according to the present invention, to be useful in the methods described herein, the use of a gene encoding a BMP8 protein obtained from any other mammalian tissue, preferably, a human tissue, is also included in the invention. Further, the invention should be construed to include nucleic acid encoding BMP8 from mammals other than humans, which BMP8 functions in a substantially similar manner to the mouse BMP8 described herein. Preferably, the nucleic acid encoding BMP8 is about 50% homologous, more preferably about 70% homologous, even more preferably about 80% homologous and most preferably about 90% homologous to the nucleic acid encoding mouse BMP8A or BMP8B.

"Homologous" as used herein, refers to the subunit sequence similarity between two polymeric molecules, e.g., between two nucleic acid molecules, e.g., two DNA molecules or two RNA molecules, or between two polypeptide molecules. When a subunit position in both of the two molecules is occupied by the same monomeric subunit, e.g., if a position in each of two DNA molecules is occupied by adenine, then they are homologous at that position. The homology between two sequences is a direct function of the number of matching or homologous positions, e.g., if half (e.g., five positions in a polymer ten subunits in length) of the positions in two compound sequences are homologous then the two sequences are 50% homologous, if 90% of the positions, e.g., 9 of 10, are matched or homologous, the two sequences share 90% homology. By way of example, the DNA sequences 3' ATTGCC 5' and 3' TATGCG 5' share 50% homology.

An "isolated nucleic acid", as used herein, refers to a nucleic acid sequence, segment, or fragment which has been separated from the sequences which flank it in a naturally occurring state, e.g., a DNA fragment which has been removed from the sequences which are normally adjacent to the fragment, e.g., the sequences adjacent to the fragment in a genome in which it naturally occurs. The term also applies to nucleic acids which have been substantially purified from other components which naturally accompany the nucleic acid, e.g., RNA or DNA or proteins, which naturally accompany it in the cell.

The invention also includes an isolated nucleic acid having a sequence which is in the antisense orientation (i.e., is complementary) to a portion or all of the nucleic acid encoding BMP8. By "complementary to a portion or all of a Bmp8 gene" is meant a sequence of nucleic acid which does not encode BMP8. Rather, the sequence which is being expressed in the cells is identical to the non-coding strand of the BMP8 gene and thus, does not encode BMP8.

The terms "complementary" and "antisense" as used herein, are not entirely synonymous. "Antisense" refers particularly to the nucleic acid sequence of the non-coding strand of a double stranded DNA molecule encoding a protein, or to a sequence which is substantially homologous to the non-coding strand. "Complementary" as used herein refers to the broad concept of subunit sequence complementarity between two nucleic acids, e.g., two DNA molecules. When a nucleotide position in both of the molecules is occupied by nucleotides normally capable of base pairing with each other, then the nucleic acids are considered to be complementary to each other at this position. Thus, two nucleic acids are complementary to each other when a substantial number (at least 50%) of corresponding positions in each of the molecules are occupied by nucleotides which normally base pair with each other (e.g., A:T and G:C nucleotide pairs). As defined herein, an antisense sequence is complementary to the sequence of a double stranded DNA molecule encoding a protein. It is not necessary that the antisense sequence be complementary solely to the coding portion of the coding strand of the DNA molecule. The antisense sequence may be complementary to regulatory sequences specified on the coding strand of a DNA molecule encoding a protein, which regulatory sequences control expression of the coding sequences.

The invention thus should be construed to include nucleic acid encoding BMP8 and fragments of nucleic acid encoding BMP8; and, nucleic acid and fragments of nucleic acid which is in the antisense orientation to nucleic acid encoding BMP8.

Fragments of nucleic acid encoding BMP8 encode portions of BMP8 which have the biological activity of BMP8 as defined herein, or which encode a polypeptide comprising a portion of BMP8, which polypeptide is useful, as discussed in detail herein, in the methods of the invention.

The invention also includes an isolated protein encoded by Bmp8 as described herein, and other BMP8 molecules encoded by other Bmp8 genes which may be isolated by the skilled artisan once armed with the present invention. Preferably, the amino acid sequence of a BMP8 protein so discovered is about 70% homologous, more preferably about 80% homologous, even more preferably about 90% homologous, more preferably, about 95% homologous, and most preferably, at least about 99% homologous to the amino acid sequence of mouse BMP8A or mouse BMP8B.

Substantially pure BMP8 protein obtained as described herein may be purified by following known procedures for protein purification, wherein an immunological, enzymatic or other assay is used to monitor purification at each stage in the procedure.

As used herein, the term "substantially pure" describes a compound, e.g., a protein or polypeptide which has been separated from components which naturally accompany it. Typically, a compound is substantially pure when at least 10%, more preferably at least 20%, more preferably at least 50%, more preferably at least 60%, more preferably at least 75%, more preferably at least 90%, and most preferably at least 99% of the total material (by volume, by wet or dry weight, or by mole percent or mole fraction) in a sample is the compound of interest. Purity can be measured by any appropriate method, e.g., in the case of polypeptides by column chromatography, gel electrophoresis or HPLC analysis. A compound, e.g., a protein, is also substantially purified when it is essentially free of naturally associated components or when it is separated from the native contaminants which accompany it in its natural state.

The present invention also provides for the use of analogs of proteins or peptides encoded by a Bmp8 gene. Analogs can differ from naturally occurring proteins or peptides by conservative amino acid sequence differences or by modifications which do not affect sequence, or by both.

For example, conservative amino acid changes may be made, which although they alter the primary sequence of the protein or peptide, do not normally alter its function. Conservative amino acid substitutions typically include substitutions within the following groups:

glycine, alanine;
valine, isoleucine, leucine;
aspartic acid, glutamic acid;
asparagine, glutamine;
serine, threonine;
lysine, arginine;
phenylalanine, tyrosine.

Modifications (which do not normally alter primary sequence) include in vivo, or in vitro chemical derivatization of polypeptides, e.g., acetylation, or carboxylation. Also included are modifications of glycosylation, e.g., those made by modifying the glycosylation patterns of a polypeptide during its synthesis and processing or in further processing steps; e.g., by exposing the polypeptide to enzymes which affect glycosylation, e.g., mammalian glycosylating or deglycosylating enzymes. Also embraced are sequences which have phosphorylated amino acid residues, e.g., phosphotyrosine, phosphoserine, or phosphothreonine.

Also included are polypeptides which have been modified using ordinary molecular biological techniques so as to improve their resistance to proteolytic degradation or to optimize solubility properties. Analogs of such polypeptides include those containing residues other than naturally occurring L-amino acids, e.g., D-amino acids or non-naturally occurring synthetic amino acids. The peptides of the invention are not limited to products of any of the specific exemplary processes listed herein.

In addition to substantially full length polypeptides, the present invention provides for biologically active fragments of the polypeptides.

A BMP8 polypeptide is "biologically active" if it adequately supports the survival of spermatocytes in the assays which are described in the experimental details section herein.

The invention also contemplates the use of BMP8 polypeptides that are either full length or are less than full length. Such fragments may be biologically active, as defined herein, or may be biologically inactive in that they do not adequately support survival of spermatocytes. In the latter instance, such fragments may be useful for inhibition of the biological activity of BMP8, when added to cells, either in vitro or in vivo. The invention also contemplates the use of mutants of BMP8, which mutants comprise one or more mutations which render the BMP8 protein inactive.

As used herein, the term "fragment," as applied to a polypeptide, will ordinarily be at least about fifteen contiguous amino acids, typically at least about twenty five contiguous amino acids, more typically at least about forty contiguous amino acids, usually at least about forty five contiguous amino acids and preferably at least about fifty contiguous amino acids in length.

DNA encoding BMP8 proteins from a mammal may be obtained following the procedures described herein using as probes in hybridization assays, PCR reactions and the like, portions of Bmp8a or Bmp8b. Essentially, DNA is extracted from cells obtained from the desired mammal. The procedures for the isolation, cloning and sequencing and other characterization of a DNA molecule are well known in the art and are described, for example, in Sambrook et al. (1989, Molecular Cloning: A Laboratory Manual, Cold Spring Harbor, N.Y.).

As the data presented herein establish, BMP8 plays at least three distinct roles in spermatogenesis. It is required for the survival of differentiating spermatocytes, for the proliferation of spermatogonial cells and for their differentiation.

Thus, it has been discovered in the present invention that administration of BMP8 to certain mammalian cells facilitates proliferation of those cells. In particular, mammalian spermatogonial stem cells are caused to proliferate in the presence of this protein. Thus, there is provided in the invention a method of proliferating mammalian spermatogonial cells. The method comprises culturing spermatogonial stem cells in the presence of BMP8 protein. The culture medium for culturing spermatogonial cells and the other conditions under which such cells are maintained are described in the experimental details section herein. Regarding the amount of BMP8 to be added to spermatogonial stem cells to effect their proliferation, it will be appreciated that the amount of BMP8 required in the method of the invention will depend upon the type of mammal from which the cells and the BMP8 are derived. Generally, BMP8 is added to cells in a concentration of between about 1 ng/ml to about 10 mg/ml of culture medium. Preferably, BMP8 is added to cells in a concentration of about 1 $\mu$g/ml to about 500 $\mu$g/ml of culture medium.

It has also been discovered in the present invention that administration of BMP8 to certain mammalian cells facilitates differentiation of those cells. In particular, mammalian spermatogonial stem cells are caused to differentiate in the presence of this protein. Whether a culture of spermatogonial cells is caused to proliferate or differentiate depends on the developmental stage of the cells at the time BMP8 is added to the culture. Thus, spermatogonial stem cells which are in one developmental stage may be caused to proliferate in response to BMP8, whereas, cells which are in another developmental stage may be caused to differentiate in the presence of BMP8. It will be apparent to the artisan skilled in spermatogonial cell development whether any particular culture of spermatogonial stem cells will undergo proliferation or differentiation in the presence of BMP8.

There is therefore also provided in the invention a method of differentiating mammalian spermatogonial cells. The method comprises culturing spermatogonial stem cells in the presence of BMP8 protein. The culture medium for culturing spermatogonial cells and the other conditions under which such cells are maintained are described in the experimental details section herein. Regarding the amount of BMP8 to be added to spermatogonial stem cells to effect their differentiation, it will be appreciated that the amount of BMP8 required in the method of the invention will depend upon the type of mammal from which the cells and the BMP8 are derived. Generally, BMP8 is added to cells in a concentration of between about 1 ng/ml to about 10 mg/ml of culture medium. Preferably, BMP8 is added to cells in a concentration of about 1 $\mu$g/ml to about 500 $\mu$g/ml of culture medium.

Regarding differentiation of spermatogonial cells using BMP8, cells which are caused to differentiate, any actually terminally differentiate and therefore undergo apoptosis. The invention thus also provides a method of inducing apoptosis of spermatocytes.

In addition to proliferation and differentiation, the addition of BMP8 to spermatogonial stem cells effects their maintenance in culture. Similar to the situation regarding proliferation and differentiation, maintenance of spermatogonial cells in culture is effected by added to the cells an amount of BMP8 protein sufficient for the maintenance of the cells. Such maintenance is referred to herein as "extending the viability" of spermatogonial cells.

In general, preparations of BMP8 which are added to cells in culture include the desired concentration of BMP8 suspended in cell culture medium or other isotonic solution which is compatible with the viability of the cells. Such solutions will be apparent to the artisan skilled in protein administration to cells for the purposes described herein.

It will be appreciated from the discussion provided herein that incubation of cells in the absence of BMP8, or in the presence of a substance which effects the substantial absence of BMP8 in the cell culture, serves to cause the cells to cease to proliferate, and/or differentiate, and/or be maintained in the culture. Such a situation provides a scenario for the study of male infertility. In addition, when practiced in vivo, as described herein, such a situation provides a method of inducing infertility in a male mammal.

Thus, according to the invention, there is provided a method of arresting the proliferation of spermatogonial stem cells in culture comprising incubating the cells in the substantial absence of BMP8.

In addition, there is provided a method of arresting the differentiation of spermatocytes in culture comprising incubating the cells in the substantial absence of BMP8.

Further, there is provided a method of arresting the maintenance of spermatocytes in culture comprising incubating the cells in the substantial absence of BMP8.

It will be appreciated that whether the property of the cell to be affected by incubation in the substantial absence of BMP8 is proliferation, differentiation or maintenance, will depend on the developmental stage of the cells. The appropriate developmental stage of the cells will be apparent to the artisan skilled in cell development.

When the method of the invention calls for the incubation of cells in the substantial absence of BMP8, this should be construed to include incubating cells in the absence of BMP8, and to include incubation of cells in the presence of BMP8 wherein BMP8 activity is inhibited by any desired means. Such inhibition means include the addition of an antibody to BMP8 to the culture; the addition of other inhibitors of BMP8 function such as small molecules and peptidometics; the inhibition of production of BMP8 protein, such as by adding antisense nucleic acids to the BMP8 mRNA using methodology well known in the art.

"Substantial absence of BMP8" means the amount of BMP8 present does not adequately support the survival of spermatocytes.

Antibodies to BMP8 may be generated using any technology well known in the art and described, for example, in Harlow et al. (1988, In: Antibodies, A Laboratory Manual, Cold Spring Harbor, N.Y.). Antibodies to BMP8 should be construed to include polyclonal, monoclonal and synthetic antibodies.

By the term "synthetic antibody" as used herein, is meant an antibody which is generated using recombinant DNA technology, such as, for example, an antibody expressed by a bacteriophage. The term should also be construed to mean an antibody which has been generated by the synthesis of a DNA molecule encoding the antibody and which DNA molecule expresses an antibody protein, or an amino acid sequence specifying the antibody, wherein the DNA or amino acid sequence has been obtained using synthetic DNA or amino acid sequence technology which is available and well known in the art.

To obtain a substantially pure preparation of a synthetic antibody, the antibody may be extracted from the surface of the phage on which it is expressed. The procedures for such extraction are well known to those in the art of protein purification. Alternatively, a substantially pure preparation of an antibody may be obtained by cloning an isolated DNA encoding the antibody into an expression vector and expressing the protein therefrom. Antibody so expressed may be obtained using ordinary protein purification procedures well known in the art. Procedures for the generation of synthetic antibodies are described in Barbas (1995, Nature Medicine 1:837–839) and in de Kruif et al. (1995, J. Mol. Biol.248:97–105) and in the refererences cited therein.

Also provided are peptidometics having BMP8 biological activity. Peptidometics having BMP8 biological activity include compounds which have a sufficient BMP8 activity such that their effects on the cells to which they are administered are beneficial to the sell, which beneficial effects are similar to that of BMP8. Peptidometics may also have additional advantages over BMP8 in that they may be designed such that they are capable of accessing targets in an animal which are normally relatively inaccessible to BMP8.

Information describing the generation, use and administration of peptidometics is provided in PCT/US93/01201 and U.S. Pat. No. 5,334,702, which are hereby incorporated herein by reference. Any of the techniques described in either of these two references may be employed in the present invention for the administration of peptidometics.

Given the findings provided herein, it will be appreciated that the invention further includes a method of identifying small molecules, nucleic acids, peptides, antibodies, hormones and other compounds which affect BMP8 activity, i.e., which compounds are agonists or antagonists of BMP8 activity.

To identify an agonist of BMP8 activity, spermatogonial cells at defined stages of differentiation are incubated in the absence of any compound as a control, in the presence of BMP8, in the presence of a test compound, or in the presence of BMP8 and the test compound. The extent of proliferation and/or differentiation of the cells is measured following the incubation period. The compound is considered to be a BMP8 agonist when the extent of proliferation and/or differentiation of the cells in the presence of the test compound is equal to or greater than the extent of proliferation and/or differentiation of the cells in the presence of BMP8. If the extent of proliferation and/or differentiation of the cells in the presence of both BMP8 and the test compound is greater than the extent in BMP8 alone, then the compound is an agonist of BMP8 which acts in synergy with BMP8.

To identify an antagonist of BMP8 activity, spermatogonial cells at defined stages of differentiation are incubated in the absence of any compound as a control, in the presence of BMP8, in the presence of a test compound, or in the presence of BMP8 and the test compound. The extent of proliferation and/or differentiation of the cells is measured following the incubation period. The compound is considered to be a BMP8 antagonist when the extent of proliferation and/or differentiation of the cells in the presence of the test compound and BMP8 is less than the extent of proliferation and/or differentiation of the cells in the presence of BMP8 alone.

Compounds which act as agonists or antagonists of BMP8 are useful for promoting fertility in a male mammal or for inducing infertility in a male mammal.

The methods of the invention are applicable to the manipulation of spermatogonial cells cultured in vitro. These methods are also applicable for the manipulation of spermatogonial cells in vivo in a mammal.

BMP8, fragments of BMP8, or agonists or antagonists thereof, may be administered to cells in vivo in an animal to effect manipulation of the cells regarding proliferation, differentiation, maintenance, or apoptosis. Protocols for treatment of mammals with BMP8, or an agonist or antagonists thereof, will be apparent to those skilled in the art and will vary depending upon the situation in the mammal to be treated. Treatment regimes which are contemplated include a single dose or dosage which is administered hourly, daily, weekly or monthly, or yearly. Dosages may vary from 1 µg to 1000 mg/kg of body weight of the agonist or antagonist, or of BMP8 and will be in a form suitable for delivery of the compound. The route of administration may also vary depending upon the disorder to be treated.

The agonist, antagonist or BMP8 is prepared for administration by being suspended or dissolved in a pharmaceutically acceptable carrier such as saline, salts solution or other formulations apparent to those skilled in such administration. The compositions of the invention may be administered to a mammal in one of the traditional modes (e.g., orally, parenterally, transdermally or transmucosally), in a sustained release formulation using a biodegradable biocompatible polymer, or by on-site delivery using micelles, gels and liposomes, or rectally (e.g., by suppository or enema) or nasally (e.g., by nasal spray). The appropriate pharmaceutically acceptable carrier will be evident to those skilled in the art and will depend in large part upon the route of administration.

For administration to the testes of an animal, the compound to be administered directly into the testes by injection or other suitable means which will be apparent to those skilled in the art.

Provided herein is a method of treating infertility in a male mammal, comprising administering to the mammal BMP8 protein, thus facilitating spermatogenesis and treating infertility. Also provided is a method of treating infertility in a male mammal, comprising administering to testis cells of the mammal BMP8 protein, thus facilitating proliferation and differentiation of the cells and treating infertility. In particular the male mammal may have a defect in spermatogenesis resulting from reduced levels of functional BMP8 protein. The BMP8 protein can be administered by administering a nucleic acid functionally encoding BMP8, thus providing BMP8 protein. Additionally, the protein can be administered by methods elaborated herein and other methods known in the art. The BMP8 protein can, for example, be injected into the rete region of the testis, thus allowing the protein to diffuse into the seminiferous tubules.

Also provided is a method of inducing infertility in a male mammal. Administration to a mammal of a substance which effects the substantial absence of BMP8 in cells in the testes, or administration to a male mammal of an antagonist of BMP8 activity will serve to reduce or eliminate BMP8 function in the cells thereby reducing or eliminating spermatogenesis in the mammal. Methods, routes and formulations for administration of BMP8 antagonists or other compounds which reduce or eliminate BMP8 activity are generally the same as the methods just described for treatment of male infertility and will be apparent to the skilled artisan once armed with the present invention.

The invention also includes a method of isolating a BMP8 receptor on a cell comprising binding BMP8 to a BMP8-responsive population of cells, and isolating the protein on the cells to which the BMP8 binds.

By "BMP-responsive population of cells" as used herein, is meant a population of cells which proliferate or differentiate in response to BMP8 in the assays described herein.

A receptor protein may be isolated using any one of a number of protein isolation techniques available in the art, including, for example, immunoaffinity techniques, other biochemical affinity techniques, and the like as described herein and as can be found in any ordinary biochemistry manual for protein purification.

To facilitate the isolation of a BMP8 receptor protein, BMP8 to be bound to the cells may be labeled with a detectable marker, it may be tagged with an identifiable marker, or it may be covalently bound (i.e., as a fusion protein) to a tag to facilitate isolation of a protein bound to it. Generation of fusion proteins for the isolation of receptor proteins is well known in the art of molecular biology.

Also provided in the invention is a method of treating a mammal for defects in embryo implantation in the uterus, comprising administering to the mammal BMP8 protein, thereby facilitating implantation. The time period for administration can preferably be when decidual cell proliferation and hypertrophy peak (Finn, 1971, Adv. Reprod. Physiol. 5:1–26)). Compounds may be administered directly to the uterine wall or administration may be effected systemically. BMP8 protein may be administered or, nucleic acid encoding BMP8 can be administered. One can modify the nucleic acid such that it is expressed at appropriate times during development of the cells to be manipulated, e.g., by using a promoter derived from a gene which is normally expressed in the desired cells at the desired time.

Also provided is a method of facilitating maintenance of the placenta of a pregnant mammal, comprising administering to the mammal a maintaining amount of BMP8 protein, thereby facilitating maintenance of the placenta. Administration of the BMP8 protein can be, e.g., by injection or direct application as described herein.

It is apparent from the data provided herein that BMP8 may have effects on cells other than spermatogonial cells, during various stages in their development. In particular, hair follicle cells are likely to be affected by BMP8, in that they are likely to be stimulated to produce hair. Thus, the invention also provides a method of stimulating hair growth in a mammal, comprising administering a stimulating amount of BMP8 to the hair follicles, thereby stimulating hair growth. Compositions can be formulated for application of the BMP8 protein to the hair follicles, which compositions comprise suitable carriers for topical delivery of the BMP8 that are known the art and are described, for example, in Martin (ed. Remington's Pharmaceutical Sciences, Mack Publishing Co., Easton, Pa.). For example, formulations such as used for the administration of minoxidol can be utilized in the method of the present invention.

Bmp8a homozygous null mice have the same phenotype as Bmp8b homozygous mutants and the expression pattern of the two genes is the same in the testis. This is evidence that the two proteins have identical functions in mammalian spermatogenesis and will be interchangeable experimentally and in therapeutically. Therefore, BMP8 protein can be used therapeutically to treat infertility and as an essential growth factor for obtaining and/or maintaining lines of spermatogonial stem cells in culture.

Based on the data provided herein concerning the effect of depriving mice of BMP8, BMP8 is useful as a therapeutic agent in the treatment of human males with infertility due to specific classes of defects in spermatogenesis in the seminiferous tubules. For example, these abnormalities could be due to intrinsic genetic defects in the Bmp8 gene (coding or non-coding sequences) or in other genes encoding proteins which regulate the expression of the Bmp8 gene. Alternatively, extrinsic hormonal or environmental factors may inactivate the Bmp8 gene or interfere with its normal regulation. The infertility of these patients may be treated by administration of BMP8 either systemically or in slow-release beads coated with or impregnated with protein. Such beads could be implanted into one or both testes. The beads coated or impregnated with BMP8 protein could also be administered from a high velocity particle "gun".

BMP8 useful in the methods of the invention may be a recombinant protein comprising dimers of the C-terminal TGFβ-like portion of the protein. This recombinant protein may be easily generated in an insect cell/bacculovirus expression system. Alternatively, COS cells may be used for generation of BMP8, which cells generally modify and process proteins for secretion in a biologically active form. Such expression systems are widely used for the production of other cytokines, including proteins related to BMP8 (e.g. BMP2 and BMP7/Osteogenic protein 1 are in preclinical trials).

In addition, a gene therapy approach using a retrovirus vector, which contains for example, but not limited to, a EF1-α promoter-driven Bmp8 gene, may be used to deliver BMP8 proteins to spermatogonia. EF1-α promoter is known to drive specific gene expression in spermatogonia in transgenic mice (Furuchi et al., 1996, Development 122:1703–1709). Furthermore, in addition to the use of viral vectors, non-viral vectors, such as, but not limited to, cationic liposomes may be used to deliver the nucleic acid to cells.

When Bmp8 nucleic acid is to be added to cells, the nucleic acid may be modified, for example, by adding nucleic acid sequences encoding signal sequences to promote secretion of the protein from cells so that surrounding cells are also affected by the protein.

BMP8 treatment may also be useful for increasing the fertility of endangered mammalian species in captivity, which animals have inefficient spermatogenesis due to hormonal or environmental factors or old age.

Transgenic animals comprising mutations in the Bmp8 gene are useful for the study of the role of BMP8 in cell development, for the identification and testing of compounds which affect BMP8 activity in vivo. The generation of such transgenic animals is described herein.

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

Methods for the Isolation, Propagation and Differentiation of Spermatogonial Stem (SS) Cell Lines from Mammalian Testis Methods have already been well established for purifying (into roughly homogenous populations) and culturing for short periods of time spermatogenic cells from rats, mice. These methods are reviewed in "Purification, culture and fractionation of spermatogenic cells" by Anthony R. Bellve in *Methods in Enzymology* 225:84–113 (1993).

BMP8 homozygous mutant mice at 1–2 weeks of age can be used to obtain populations of cells highly enriched in the most primitive spermatogonial stem (SS) cells which are normally very hard to obtain because they form a very small proportion of the total spermatogenic cells of the testis.

The isolated cell population enriched in stem cells is then cultured in a culture dish (collagen coated) either alone or in the presence of inactivated feeder cells ( to mimic the supportive function of Sertoli cells) in the presence of culture medium containing low levels of serum (1–10%) and different levels of BMP8 protein (these levels could range from 0.5 to 500 ng/ml). Addition of other growth factors in the same concentration range may also be used, for example fibroblast growth factor (FGF), Steel factor, LIF, Interleukins, nerve growth factor, activin. Fibroblast growth factor is known to be expressed in spermatogonial cells in the rat and mouse. Combinations of different classes of growth factors ( LIF, Steel Factor and FGF) may be beneficial as found for the culture of cell lines from primordial germ cells in the fetal gonad.

Until the present invention, spermatogonia only remained viable in culture for 24–48 hours. According to the present invention, the addition of BMP8 alone, or in combination with other factors, overcomes this block and allow the cells to continue proliferating indefinitely.

The methods described herein apply to human testes either from newborn or very young males (donated after death) or from adult males. Alternatively, cells may be isolated from the subject utilizing techniques currently used to obtain cells from testes for microinjection into eggs for fertilization. These procedures are in the art of fertility testing and include, for example, needle biopsy of the testis.

Testes cells so obtained, are dissociated and cultured in the presence of a cocktail of growth factors to stimulate the proliferation of SS cells.

Additional methods for obtaining testes cells are as follows: Testes are dissected and the tunica removed. The testes are then incubated at 32° C. with mild shaking in buffered saline containing bovine serum albumin and collagenase (final concentration approximately 0.5 mg/ml). When the tissue has dissociated the tubules are allowed to settle out and then washed in saline several times. The collagenase treatment is repeated to remove all the cells surrounding the tubules (Leydig cells and connective tissue). The tubules are then washed and treated with hyaluronidase in buffered saline (final concentration approximately 0.5 mg/ml) at 32° C. until the tubules are free of adherent material. The tubules are washed and placed onto tissue culture dishes coated with Poly-L-lysine. The Sertoli cells attach strongly to the dish and spread out, while the germ cells remain in suspension. The germ cells are collected and plated onto a layer of irradiated feeder cells comprising membrane bound and soluble stem cell factor, LIF and basic FGF as described in U.S. Pat. No. 5,453,357, which is incorporated by reference.

A "pluripotential embryonic stem cell" as used herein means a cell which can give rise to many differentiated cell types in an embryo or adult, including the germ cells (sperm and eggs). Pluripotent embryonic stem cells are also capable of self-renewal. Thus, these cells not only populate the germ line and give rise to a plurality of terminally differentiated cells which comprise the adult specialized organs, but also are able to regenerate themselves. This cell type is also referred to as an "ES cell" herein.

A "fibroblast growth factor" (FGF) as used herein means any suitable FGF. There are presently seven known FGFs. These FGFs include FGF-1 (acidic fibroblast growth factor), FGF-2 (basic fibroblast growth factor), FGF-3 (int-2), FGF-4 (hst/K-FGF), FGF-5, FGF-6, FGF-7 and FGF-8.

Each of the suitable factors may be used directly in the methods taught herein to produce or maintain ES cells. Each FGF can be screened in the methods described herein to determine if the FGF is suitable to enhance the growth of or allow continued proliferation of ES cells or their progenitors. Various examples of FGF and methods of producing an FGF are well known; see, for example, U.S. Pat. Nos. 4,994,559; 4,956,455; 4,785,079; 4,444,760; 5,026,839; 5,136,025; 5,126,323; and 5,155,214.

"Steel factor" (SF) is used herein. SF is also called stem cell factor, mast cell growth factor and c-kit ligand in the art. SF is a transmembrane protein with a cytoplasmic domain and an extracellular domain. Soluble SF refers to a fragment cleaved from the extracellular domain at a specific proteolytic cleavage site. Membrane associated SF refers to both normal SF before it has been cleaved or the SF which has been altered so that proteolytic cleavage cannot take place. SF is well known in the art; see European Patent Publication No. 0 423 980 A1, corresponding to European Application No. 90310889.1.

"Leukemia Inhibitory Factor" (LIF) is also used herein. LIF is also known as DIA or differentiation inhibiting activity. LIF and uses of LIF are also well known; see for example U.S. Pat. Nos. 5,187,077 and 5,166,065.

It should be recognized that BMP8, FGF, SF and LIF are all proteins and as such certain modifications can be made to the proteins which are silent and do not remove the activity of the proteins as described herein. Such modifications include additions, substitutions and deletions. Methods modifying proteins are well established in the art (Sambrook et al., *Molecular Cloning: A Laboratory Manual,* 2nd Ed., Cold Spring Harbor Laboratory, Cold Spring Harbor, N.Y., 1989).

Once the ES cells are established, they can be genetically manipulated to produce a desired characteristic. For example, the ES cells can be mutated to render a gene non-functional, e.g. oncogene. Alternatively, functional genes can be inserted to allow for the production of that gene product in an animal, e.g. growth hormones or valuable proteins.

Proliferating-enhancing amounts of FGF, LIF and SF can vary depending on the species or strain of the cells, and type or purity of the factors. Generally, 0.5 to 500 ng/ml of each factor within the culture solution is adequate. In a more narrow range, the amount is between 10 to 20 ng/ml for βFGF and LIF and between 10 to 100 ng/ml for SF. Regardless of whether the actual amounts are known, the optimal concentration of each factor can be routinely determined by one skilled in the art. Such determination is performed by titrating the factors individually and in combination until optimal growth is obtained. Additionally, other factors can also be tested to determine their ability to enhance the effect of FGF, LIF and SF on ES cell proliferation. As described below, such other factors, or combinations of factors when used to enhance ES cell proliferation can be included within the above compositions. Also, compounds and fragments of FGF, LIF and SF which mimic the function of these factors can be used to enhance the growth and proliferation of the cells to become ES cells and are included within the scope of the invention.

The invention thus provides a method of making a mammalian pluripotential embryonic stem cell comprising incubating a population of cells from postnatal mammalian testis comprising spermatogonial stem cells in the substantial absence of BMP8, then incubating the resulting population of cells in a composition comprising a growth enhancing amount of basic fibroblast growth factor, leukemia inhibitory factor, membrane associated steel factor, and soluble steel factor, thereby making a pluripotential embryonic stem cell from a spermatogonial stem cell. In the testis, these spermatogonial stem cells represent a small population of cells capable of both self-renewal and differentiation into mature spermatogonia.

These methods may be practiced utilizing any animal cell, especially mammal cells including mice, rats, rabbits, guinea pigs, goats, cows, pigs, humans, etc. The ES cell produced by this method is also contemplated.

Additional growth factors may be found useful in enhancing the production and proliferation of germ cells from various animals.

The Methods used in the next set of experiments presented herein are now described.

Isolation of Bmp8b Genomic DNA and cDNA

Figure 3B:
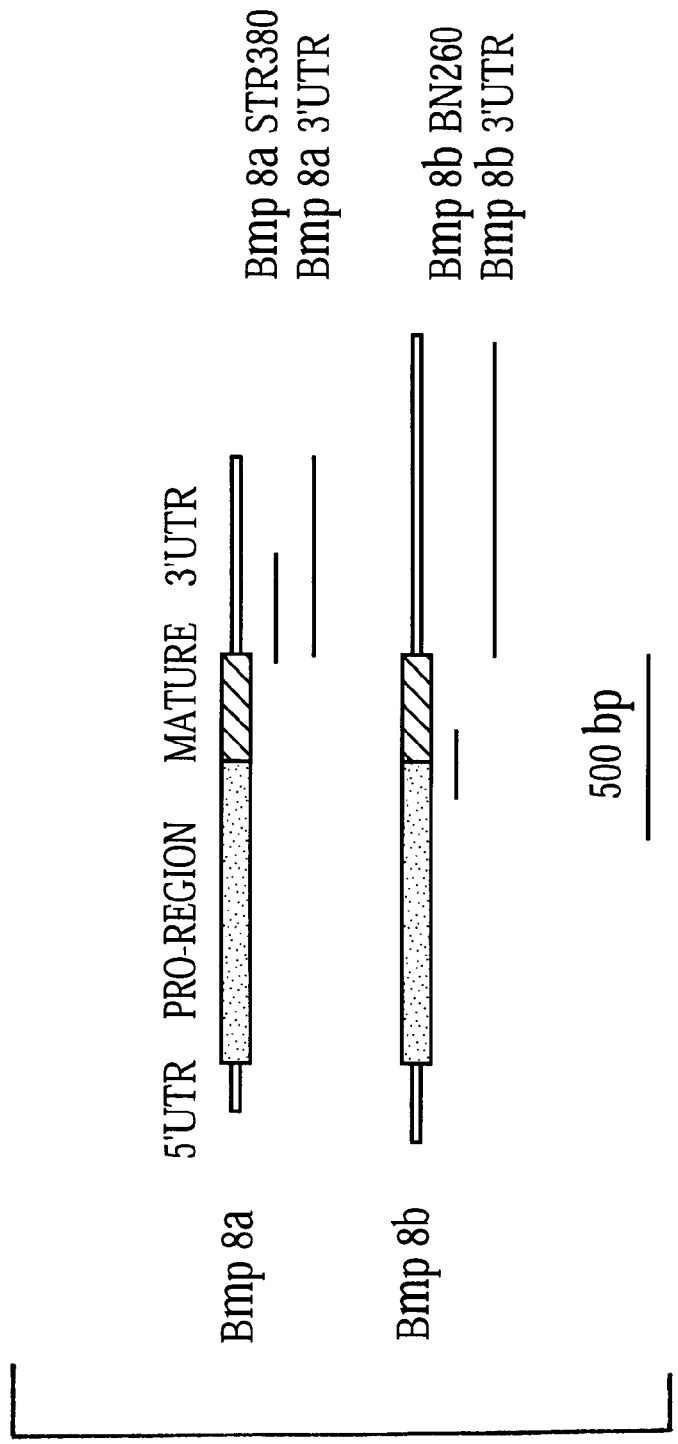
FIG. 3B is a schematic representation of Bmp8a and Bmp8b cDNAs. The coding regions, including the pro-region and mature region, are boxed. Regions used in DNA constructs for the generation of riboprobes are indicated.

Approximately $5 \times 10^5$ phage plaques of a 129/SvJ mouse genomic DNA library in lambda Fix II (Stratagene) were spread on NZY-agar plates and transferred to Hybond positively charged nylon membranes (Amersham Life Science). Hybridization was done overnight at 65° C. in 0.5 M $NaH_2PO_4$ (pH 7.2), 7% sodium dodecyl sulfate (SDS), 3 mM EDTA with a mouse Bmp8a cDNA probe (containing exons 2–7; Özkaynak et al., 1992, J. Biol. Chem. 267:25220–25227). Final washing was carried out at 65° C. in 0.2×SSC, 0.2% SDS for 30 minutes. Two overlapping clones of Bmp8a and seven overlapping Bmp8b clones were isolated. Bmp8b cDNAs were isolated by 5' and 3' RACE-PCR (Frohman et al., 1988, Proc. Natl. Acad. Sci. USA 85:8998–9002; Loh et al., 1989, Science 243:217–220; Bertchtold, 1989, Nucleic Acids Res. 17, 453) with total RNA obtained from 14.5 d.p.c. placenta. Gene specific primers were derived from exon 4 encoding part of the mature region of Bmp8b (FIG. 3B, Bmp8b BN260). DNA sequencing was performed by the dideoxynucleotide termination method (Sanger et al., 1977, Proc. Natl. Acad. Sci. USA 74:5463–5467).

Chromosome Mapping

A 2.0 kb SalI-EcoRI Bmp8a genomic DNA fragment downstream of exon 7 was used as a probe for Southern blot at high stringency. Restriction fragment length variants (RFLVs) were found with MspI digested C57BL/6J (2.7 kb) and *Mus spretus* (4.0 kb) genomic DNA. A 1.4 kb XbaI Bmp8b genomic DNA fragment from intron 6 was used as a probe for Southern blot at high stringency. RFLVs were also found with MspI digested C57BL/6J (4.1 kb) and *Mus spretus* (1.5 kb and 0.5 kb) genomic DNA. Both probes were hybridized with The Jackson Laboratory interspecific backcross DNA panel (C57BL/6JEi x SPRET/Ei) F1 x SPRET/Ei (Rowe et al., 1994, Mamm. Genome 5, 253–274) digested with MspI. Both genes were mapped to mouse chromosome 4 and no recombination event occurred between these two genes in this panel of 94 DNA samples. The mapping data have been submitted to the Jackson Laboratory Backcross Data on the World Wide Web at htt://www.jax.org/resources/documents/cmdata.

DNA Constructs

Bmp8a STR380 (FIG. 3B) was constructed by inserting a 380 bp Bmp8a cDNA fragment (from base pair 1273 to 1653, Özkaynak el. al., 1992, J. Biol. Chem. 267:25220–25227) into pBluescript KSII between SmaI and EcoRI. Bmp8b BN260 was made by inserting a 260 bp genomic DNA fragment containing exon 4 into pBluescript KS II (Stratagene). Bmp8a 3' UTR and Bmp8b 3' UTR (FIG. 3B) were constructed by inserting the 600 bp and 900 bp 3' UTRs of each gene (generated by RT-PCR) into pBluescript SKII (Stratagene).

Preparation of RNA and RNase Protection Assays

Total RNA from mouse tissues and embryos was isolated by guanidine thiocyanate-cesium chloride ultracentrifugation and phenol/chloroform extraction. RNase protection assays were performed with 10 μg total RNA from each tissue. Antisense RNA probes labeled with $^{32}$p were synthesized using T3 or T7 RNA polymerase and template DNAs Bmp8a STR380, Bmp8b BN260, and pTRI-B-actin-mouse plasmid (Ambion). Full length probes were purified on 5% polyacrylamideurea gels. RNase protection assays were carried out with RPAII kit (Ambion).

In situ Hybridization

In situ hybridization was performed essentially as described by Zhao et al., (1993, Proc. Natl. Acad. Sci. USA 90:8633–8637) with slight modifications as follows. Freshly dissected mouse embryos and tissues were rinsed in phosphate-buffered saline (PBS), then fixed in freshly prepared 4% paraformaldehyde-PBS for 2–12 hours depending on the mass of the tissues. After fixation, the tissues were rinsed in PBS and dehydrated in a series of increasing concentrations of ethanol for a period of 3–5 hours. After being embedded in paraplast, tissues were sectioned at 7 μm. RNA probes were labeled with [a-$^{35}$S] UTP to a specific activity of $1.2 \times 10^9$ cpm/μg. Hybridization was carried out at 50–55° C. with $2 \times 10^4$ cpm/μl riboprobe for 12–16 hours in 50% formamide, 300 mM NaCl, 10 mM Tris (pH 7.4), 10 mM $NaH_2PO_4$ (pH 6.8), 5 mM EDTA (pH 8.0), 0.2% Ficoll 400, 0.2% polyvinyl pyrrolidone, 10% dextran sulfate, 200 μg/ml yeast tRNA, and 50 mM dithiothreitol (DTT). Two 30 minute high-stringency washes were carried out in 2×SSC, 50% formamide at 60–65° C. Slides were dipped in NTB-2 Kodak emulsion, then exposed for 5–14 days at 4° C. After being developed and fixed, slides were stained in Mayer's hematoxylin (Sigma) for 3–5 minutes and then mounted with permount for photography.

Generation of Deciduoma

Pseudopregnant ICR females were generated by mating females in oestrus with vasectomized males. Four days later, 50 μl mineral oil was injected into one uterus horn. Five days after injection, animals were sacrificed. Uterus and/or deciduoma were dissected out for fixation or RNA preparation.

Sequence Comparison and GenBank Accession Number

Sequence comparison between Bmp8a and Bmp8b cDNAs and proteins was performed with the BLAST program of the National Center for Biotechnology Information. The Bmp8b cDNA sequence has been submitted to GenBank under accession number U39545.

Generation of Mutant Mice

Mice with mutations in Bmp8a and Bmp8b genes have been made using the technique of homologous recombination in embryonic stem (ES) cells. In these mice, DNA sequences encoding specific protein sequences have been deleted and the genes have been rendered nonfunctional.

Bmp8a and Bmp8b genomic DNA clones from a 129/SvJ mouse genomic library were isolated. Replacement targeting constructs for Bmp8a and Bmp8b were generated. Targeting DNA constructs were transfected into 129/WvJ embryonic stem (ES) cells and targeted ES cell clones were selected by positive and negative drug selections. Targeted ES cells were injected into mouse blastocysts to generate chimeric animals (chimeras). Chimeras were mated with wildtype (+/+) Blackswiss females for germ line transmission, i.e. to obtain heterozygous (+/−) animals. Heterozygous (+/−) animals were mated to obtain homozygous (−/−) mutant animals.

Phenotype of the Mutant Mice

Male mice homozygous for a null mutation in Bmp8b have small testes and are infertile by 3 months of age. Analysis of the seminiferous tubules of adult homozygous mutants shows a very high incidence of apoptosis among the spermatocytes, establishing that the gene product (BMP8B protein) is required for the survival of these cells in vivo. Homozygous mutant mice also have delayed onset of spermatogenesis in the seminiferous tubules after birth. At one and two weeks of age the seminiferous tubules consist only of a simple layer of spermatogonial cells in contact with the basal lamina and the Sertoli cells. Studies on the rate of cell proliferation by BrdU labeling of whole animals at 1 and 2 weeks of age has established that the proliferation of spermatogonial stem cells adjacent to the basal lamina of the seminiferous tubules is greatly reduced in mutant mice. This establishes that the Bmp8b gene product also plays a crucial role in enhancing/promoting/stimulating the proliferation of spermatogonial cells after birth.

The Results of these experiments are now described.

Analysis of the Temporal and Spatial Expression of the Genes Encoding BMP8.

The experiments which are now described feature an analysis of the temporal and spatial expression of the gene encoding BMP8 (Kingsley, 1994, Genes Dev. 8:133–146), also known as osteogenic protein 2 (OP2) (Özkaynak et al., 1992, J. Biol. Chem. 267:25220–25227).

Molecular Cloning of Bmp8b

A mouse Bmp8a cDNA fragment containing exons 2 –7 was used to screen a mouse 129/SvJ genomic DNA library in lambda FixII at high stringency. Nine positive clones were purified from 5×10$^5$ plaques. Two overlapping clones corresponded to Bmp8a, starting from the middle of intron 1 and ending downstream of exon 7. The seven remaining clones were derived from a different genomic locus. Sequence analysis revealed that the new locus, Bmp8b, contained DNA sequences with a high degree of identity to those of Bmp8a. Based on the sequence information in the mature region of the presumed exon 4, specific oligonucleotide primers were designed 5' RACE- and 3' RACE-PCR was conducted using RNA isolated from 14.5 d.p.c. placenta to isolate Bmp8b cDNAs. A comparison of the deduced amino acid sequences of BMP8A and BMP8B is shown in FIG. 1.

Bmp8 Genes Share High Levels of Sequence Identity

Sequence identity between Bmp8a and Bmp8b at the nucleotide level is limited to the coding region plus about 20 flanking base pairs in both the 5' untranslated region (UTR) and the 3'UTR. DNA sequences encoding the pro-region share 91% identity while sequences encoding the mature region share 83% identity. As shown in FIG. 1, both BMP8A and BMP8B proteins contain 399 amino acids. The amino acid sequences in the pro-region of these proteins share 87% identity, while those of the mature region share 76% identity. This is exceptional among all the known closely related TGF-β superfamily members, wherein the pro-regions have higher sequence identity than the mature regions. The sequence homology of mouse BMP8 proteins with other TGF-β superfamily members is significantly lower than the homology shared between BMP8A and BMP8B.

Bmp8a and Bmp8b are Closely Linked on Chromosome 4

The Jackson Laboratory interspecific backcross panel (BSS) was used to map the chromosomal localizations of Bmp8a and Bmp8b. RFLVs between C57BL/6 and *Mus spretus* were identified for each gene using probes derived from a Bmp8a DNA fragment downstream of the 3' UTR (exon 7) or from a Bmp8b DNA fragment in intron 6. In the case of both genes, RFLVs were detected using the restriction enzyme MspI. In both cases, 94 of the (C57BL/6JEi x SPRET/Ei) F1 x SPRET/Ei backcross progeny were typed for inheritance of the *Mus domesticus* or *Mus spretus* alleles and the distribution pattern of each allele was used to place the locus onto the interspecific map (Rowe et al., 1994, Mamm. Genome 5:253–274). As shown in FIG. 2, both genes were assigned to chromosome 4, there being no recombination in 94 animals with the marker D4Mit11. These data establish that Bmp8a and Bmp8b are closely linked and suggest that these genes arose by duplication of a single gene.

The location of the two Bmp8 genes on chromosome 4 according to The Jackson Laboratory backcross panel data is compared with the composite chromosome 4 map in the Mouse Genome Database (MGD) in FIG. 2A. The only potential candidate for a mutation in Bmp8a/b is sks (skeletal fusions with sterility) (Handel et al., 1988, Gamete Res.21:409–423). In males homozygous for this recessive mutation, the majority of germ cells are arrested in late stages of meiosis.

Expression of Bmp8 Genes During Development

To investigate the function of the Bmp8 genes, the expression pattern of the genes was examined during mouse embryogenesis using a battery of techniques including Northern blotting, RNase protection assays (FIG. 3), whole mount in situ hybridization, in situ hybridization of sections (7.5–10.5 d.p.c. in FIG. 4), and screening of a 8.5 d.p.c. mouse embryo cDNA library. No detectable levels of Bmp8 expression in embryos at any of these stages were observed. These data therefore contradict a previous report wherein high levels of Bmp8a (Op2) transcripts were detected in 8.5 and 10.5 d.p.c. mouse embryos by Northern hybridization ( Özkaynak et al, supra). However, when reverse transcriptase PCR (RT-PCR) was performed using RNAs isolated from uterus and placenta of different stages, high levels of Bmp8a transcripts were detected in both tissues, and Bmp8b was detected in placenta only. RNase protection assays using RNAs from these tissues and from embryos (FIG. 3) confirmed the results obtained using RT-PCR.

To localize Bmp8 transcripts in placenta and uterus, in situ hybridization was performed using antisense RNA probes corresponding to the unique 3' untranslated region of Bmp8 mRNAs. As shown in FIG. 4, high levels of Bmp8a transcripts were detected in decidual cells between 7.5 and 10.5 d.p.c. Lower levels of expression were also detected in trophoblast cells (FIGS. 4D, 4G, and 4J). Although very low levels of Bmp8a transcripts were found by RT-PCR in the nonpregnant uterus, no strong in situ hybridization signal was observed in 5.5 d.p.c. deciduum and uterus. Therefore, expression of Bmp8a increases significantly between 5.5 and 7.5 d.p.c. Bmp8a transcripts decrease to levels undetectable by in situ hybridization after 11.5 d.p.c.

The highest levels of Bmp8a expression were observed in the antimesometrial region of the deciduum, and a decreasing gradient was noted mesometrially before 9.5 d.p.c. At 10.5 d.p.c., although the overall level of expression decreased, the highest expression was found in the mesometrial region. Bmp8a expression in decidual cells is independent of embryo implantation. This was determined by injecting mineral oil into the uteri of pseudopregnant mice to generate deciduomas in the absence of an embryo. Bmp8a expression in the deciduoma faithfully reflected the normal expression pattern after embryo implantation.

Bmp8b transcripts were detected predominantly in trophoblast cells in the labyrinthine region of the placenta starting at about 9.5 d.p.c., and transcripts were still detectable at 16.5 d.p.c. Although a very low level of Bmp8b transcripts seemed to be present in 13.5 and 15.5 d.p.c. embryos by RNase protection assays, transcripts could not be detected in the embryo proper by in situ hybridization.

Expression of Bmp8 Genes in Male Germ Cells

Among the adult tissues assayed by RNase protection including heart, brain, lung, kidney, liver, spleen, thymus, skin, skeletal muscle, testis, and ovary, only testis contained detectable Bmp8 signals. Therefore, in situ hybridization using $^{35}$S-labeled antisense RNA probes was performed on testis sections. During mammalian spermatogenesis, the early spermatogonia (stem cells) divide mitotically to give rise to primary spermatocytes. These cells in turn give rise to secondary spermatocytes and spermatids through meiosis. As reviewed in Russell et al. (1990, In:Histological and histopathological evaluation of the testis, Cache River Press, Clearwater, Fla., pp. 119–161), during mouse spermatogenesis the seminiferous tubules, which contain germ cells and somatic Sertoli cells, are arbitrarily divided into 12 stages indicated by Roman numerals. In this staging system, the morphology of acrosomes (stained by periodic acid and Schiff's reagents) and nuclei (stained with hematoxylin) of the spermatids serve as critical markers. The development of spermatids is divided into 16 stages indicated by Arabic numerals. Strictly regulated cellular associations among germ cells of different stages can be observed in different regions of the seminiferous tubules. As shown in FIG. 5, transcripts specifying both Bmp8 genes were detected in stage 6–8 round spermatids in a similar temporal and spatial pattern. Strong hybridization signals first appeared in testes of 3 week-old animals, a time when round spermatids first differentiated to stage 6. Weak signals were also detected in some pachytene spermatocytes in the testes of younger animals before 6 weeks of age ( as shown in FIG. 5, Panels M and N). The strongest hybridization signals were observed in late stage 7 and early stage 8 round spermatids and signals decreased dramatically when spermatids started to elongate (stage 9).

Among all of the known closely related members of the TGF-β superfamily of proteins, BMP8A and BMP8B exhibit the highest levels of sequence identity, especially in the pro-region. The two genes encoding these proteins are closely linked on mouse chromosome 4 and share a similar genomic organization (intron/exon size and boundaries), suggesting that they arose by a recent gene duplication. However, although their expression patterns are similar, they are not identical. In male germ cells, both genes are expressed at the highest levels in stage 6–8 round spermatids and at lower levels in pachytene spermatocytes. In the developing uterus and placenta, Bmp8a is expressed at high levels in decidual cells and at low levels in trophoblast cells, and its expression decreases to a level undetectable by in situ hybridization after 11.5 d.p.c. In contrast, Bmp8b is not expressed in the maternal component of the placenta but in the labyrinthine region of trophoblasts, where its expression persists up to at least 16.5 d.p.c. Another difference in Bmp8a and Bmp8b expression patterns is that Bmp8a is expressed at high levels in the developing hair follicles of early postnatal animals while Bmp8b is only expressed at a level slightly above background. Such differences in expression patterns suggest that following duplication of Bmp8a and Bmp8b genes, regulatory elements outside the coding exons have diverged, allowing some elements to be lost and/or others to be gained.

BMPs and Placental Development

The roles of BMPs during implantation and placental development have not been well established, although transcripts for Bmp2, Bmp4, Bmp6 (Lyons et al., 1990, Development 109:833–844) and Bmp8a and Bmp8b have all been detected in extra-embryonic sites by in situ hybridization. The expression of Bmp8a described here overlaps with that of Bmp2. High levels of both transcripts are present in the deciduum, not at the time of implantation, but rather when decidual cell proliferation and hypertrophy peak (for review Finn, 1971, Adv. Reprod. Physiol. 5:1–26). Bmp8a expression decreases when the growth of the deciduum slows down. This temporal and spatial pattern suggests that these ligands are involved in promoting the proliferation, survival and/or differentiation of the uterine stromal cells.

In the placenta, the trophoblast cells in the labyrinthine region are a relatively undifferentiated and rapidly proliferating population which gives rise to the cells in the spongiotrophoblast layer. The outer layer of spongiotrophoblast cells further differentiate into non-dividing trophoblast giant cells (Billington, 1971, Adv. Reprod. Physiol. 5:27–66; Cross et al., 1994, Science 266:1508–1518). The expression of Bmp8b is highest in the labyrinthine trophoblast region while that of Bmp4 is highest in the spongiotrophoblasts. This finding suggests that Bmp8b and Bmp4 may promote the proliferation/survival of trophoblast cells and/or regulate their differentiation into spongiotrophoblasts and ultimately into giant trophoblasts.

In the past few years, a number of genes encoding transcription factors have been detected in the trophoblast cells of the developing placenta (for review see Cross et al. 1994, Science 266:1508–1518). Among these gene products, the evidence suggests that helix-loop-helix (HLH) transcription factors, Mash-2 (Johnson st al., 1990, Nature 346:858–861), Id-1, Id-2 (Cross et al., 1994, Science 266, 1508–1518; Evans et al., 1993, Dev. Biol. 159, 485–499; Janaypour et al., 1994, Mol.Biol.Cell. 5:(suppl.), 453a), and Hxt (Cross et al.,1995, Development 121:2513–2523) affect the proliferation and differentiation trophoblasts. The newly identified eHand transcripts were also detected at high levels in the trophoblast lineage (Cserjesi et al., 1995, Dev. Biol. 170:664–678). The expression of BMPs and HLH proteins in the placenta may reflect complex interactions among these two groups of proteins in regulating the growth and differentiation of the placenta. The fact that BMP purified from bone matrix inhibits differentiation of myoblastic cells by suppressing the expression of MyoD family of HLH proteins (Murray et al., 1993, J. Cell. Biochem. 53:51–60) supports such a hypothesis.

The role of BMP8 Proteins in Spermatogenesis

Bmp8 genes are the first of the TGF-β superfamily members shown to be expressed in male germ cells. In the testes of young animals before any round spermatids appear, Bmp8 transcripts were detected in the primary spermatocytes at low levels (FIG. 5, Panels M and N for testis of 3.5 weeks). When round spermatids develop to stages 6–8, much higher levels of expression of Bmp8a and Bmp8b were detected in these haploid germ cells (FIG. 5M and N). Such an expression pattern is distinct from those of three other known TGF-β superfamily members, Müllerian inhibiting substance (MIS), inhibin, and activin, which are all expressed predominantly in the Sertoli cells of the testis. Furthermore, inactivation of these genes by targeted mutagenesis does not lead to a primary defect in male germ cells (Behringer et al., 1994, Cell 79, 415–425; Matzuk et al., 1992, Nature 360:313–319; Vassalli et al., 1994, Genes Dev. 8: 414–427; Matzuk et al., 1995, Nature 374:354–356). Rather, tumorigenesis of interstitial cells in the homozygous inhibin null mutants supports an indirect role of inhibin in testis function by inhibition of follicle stimulating hormone (FSH) production in the pituitary gland. In the absence of inhibin, the over production of FSH causes the over proliferation and tumorigenesis of the interstitial cells (Matzuk et al., 1992, supra). In the absence of MIS, the development of the female reproduction system is not fully inhibited in male mice. Although the presence of both male and female reproduction systems in the male imposes anatomical incompatibility and infertility, spermatogenesis seems relatively unaffected (Behringer et al., 1994, Cell 79, 415–425). In the absence of activin BB subunit, spermatogenesis is normal (Vassalli, et al., supra), while the absence of activin BA subunit leads to perinatal lethality, so that its role in spermatogenesis cannot be evaluated (Matzuk et al., 1995, Nature 374:354–356). However, the absence of the activin receptor ActRcII only causes a reduction in the volume of seminiferous tubules, but no primary defects in the germ cell population, suggesting that this receptor may affect the proliferation and differentiation of somatic Sertoli cells (Matzuk et al., 1995, Nature 374, 356–359).

In contrast to other TGF-β superfamily members, the data presented herein establish that the expression of the Bmp8 genes in male germ cells tightly correlates with the progression of spermatogenesis. During postnatal development of the testis, germ cells may have one of two fates, differentiation to give rise to mature sperm or degeneration either through necrosis or apoptosis. About 50% of early germ cells die during their life time, predominantly by apoptosis (Allan et al., 1987, In Potten, C. S. (Ed.), Perspectives on mammalian cell death, Oxford University Press, London. pp. 229–258; Allan et al., 1992, Cell Prolif. 25:241–250). The data presented below confirm that before puberty a significant proportion of mouse gonocytes degenerate through apoptosis. However, with the appearance of stages 6–8 round spermatids, the levels of Bmp8 expression increase (3.5 weeks of age or older) and the number of apoptotic germ cells decreases. Such an inverse relationship between the level of Bmp8a and Bmp8b expression and germ cell apoptosis favors a role of BMP8 in inhibiting germ cell degeneration. Furthermore, in the homozygous null Bmp8B mutant males, increased apoptosis of germ cells leads to testis degeneration and infertility, and eventually only Sertoli cells are left in the seminiferous tubules. These observations suggest a non-redundant role of BMP8A and BMP8B in the survival of germ cells by inhibiting apoptosis.

Expanding upon the experiments just described, in the next set of experiments the in vivo functions of Bmp8 genes was investigated using a molecular genetic approach by introducing targeted mutations into each gene separately. As discussed herein, in the absence of a functional Bmp8b gene, male germ cell proliferation is significantly reduced during early puberty, and there is also a marked increase in male germ cell apoptosis in the adult. Eventually, the majority of the Bmp8b homozygous mutant males show severe seminiferous tubule degeneration and become sterile. Therefore, Bmp8b is required both for the initiation and maintenance of spermatogenesis in the mouse. To similarly investigate the in vivo function of Bmp8a during spermatogenesis and pregnancy, the mouse gene was inactivated by homologous recombination in embryonic stem (ES) cells. The data which are now described relate to a detailed phenotypic analysis of Bmp8a mutant mice and Bmp8a/Bmp8b compound heterozygous mice. To summarize the results to be presented, the mouse Bmp8a gene is not essential for deciduum formation and placenta development and is not required for the initiation of spermatogenesis. Rather, it appears to play a role in maintaining normal spermatogenesis and the integrity of the epididymis during male reproduction.

The Methods used in the next set of experiments are now described.

Construction of the Targeting Vector

Figure 6A:
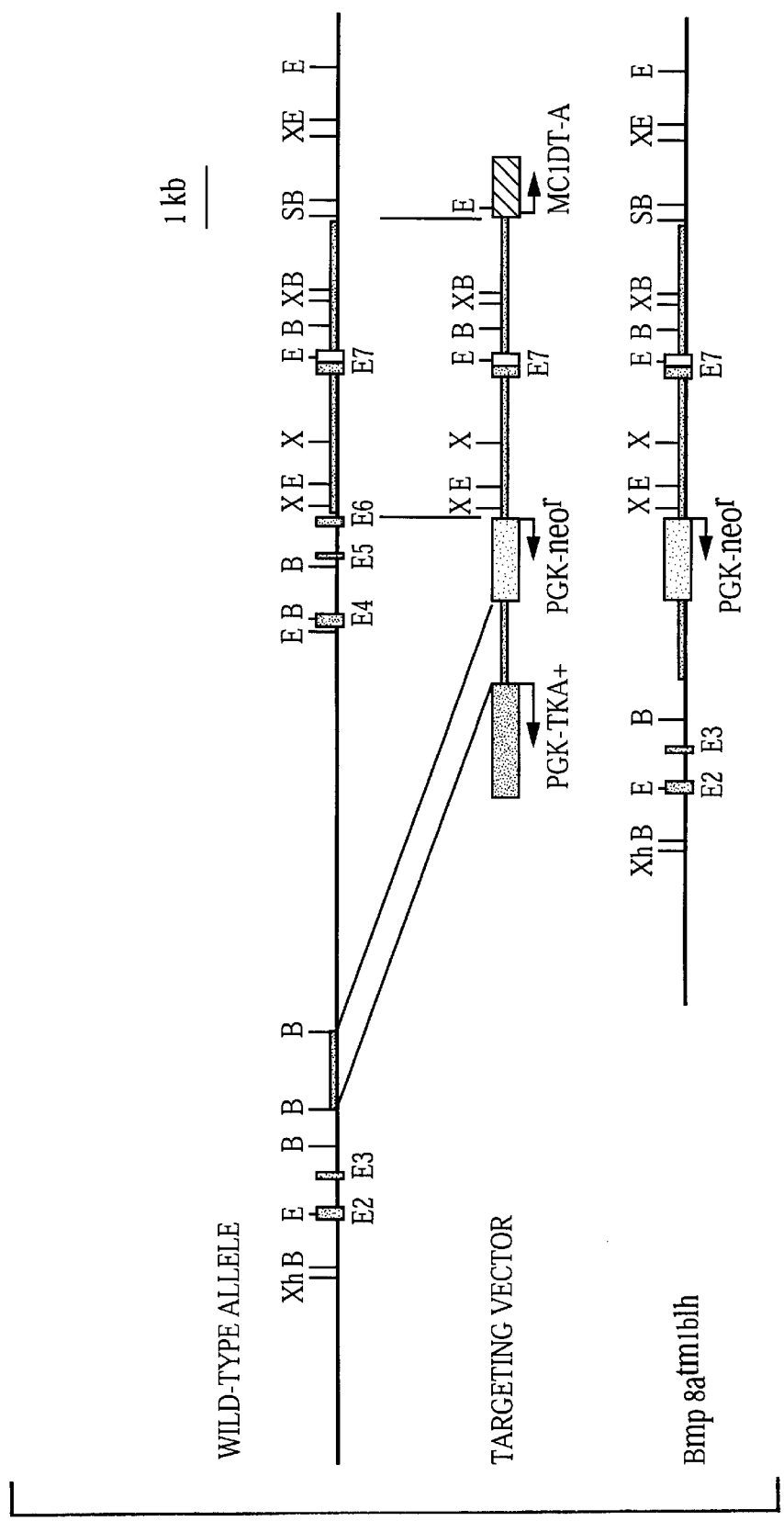
FIGS. 6A, 6B, and 6C, is a diagram depicting targeted mutagenesis of the mouse Bmp8a locus.

Bmp8a genomic DNA clones were isolated as described herein. Two overlapping Bmp8a genomic clones covering exons 2–7 were mapped by restriction enzyme digestion as shown in FIG. 6A. A replacement targeting vector was constructed using 1.2 kb 5' and 4.5 kb (5' portion of the second phage clone) 3' homology arms as indicated. As described herein, PGK-TKA+(Rudnicki, et al., 1992, Cell 71:383–390), and MCLDT-A (Yagi et al., 1990, Proc. Natl. Acad. Sci. USA 87:9918–9922) cassettes were attached to the 5' and 3' ends of the targeting vector for negative selection. In the targeted allele, exons 4–6 are deleted and replaced with PGK-neo$^r$ cassette (Rudnicki, et al., supra). This Bmp8a mutant allele is designated as Bmp8$^{atm1blh}$ according to standard nomenclature (Davisson 1995, In: Trends in Genetics Nomenclature Guide, Ed. Stewart, pp. 35–38. Elsevier Trends Journals, Kidlington, Oxford, UK).

Generation of Recombinant ES Cell Clones and Mouse Chimeras

TL1 ES cells of passage 11 and 12 were transfected with 20–50 μg of the linearized targeting vector by electroporation as described herein. ES cell culture and drug selection were performed essentially as described (Winnier et al., 1995, Genes Dev. 9:2105–2116). Three out of one hundred drug-resistant ES clones designated as A5, H4, and H9, exhibited a correctly recombined Bmp8$^{atm1blh}$ allele. All three lines were injected into C57BL/6 blastocysts to generate chimeras (Hogan et al., 1994, Manipulating the mouse embryo: A Laboratory Manual. Second edition. Cold Spring Harbor Laboratory Press, N.Y.). Bmp8$^{atm1blh}$ was transmitted from A5 and H4 cells by mating male chimeras with Black Swiss females (Taconic). Agouti animals were genotyped by Southern blotting.

Southern Blot Analysis

Figures 6B, 6C:
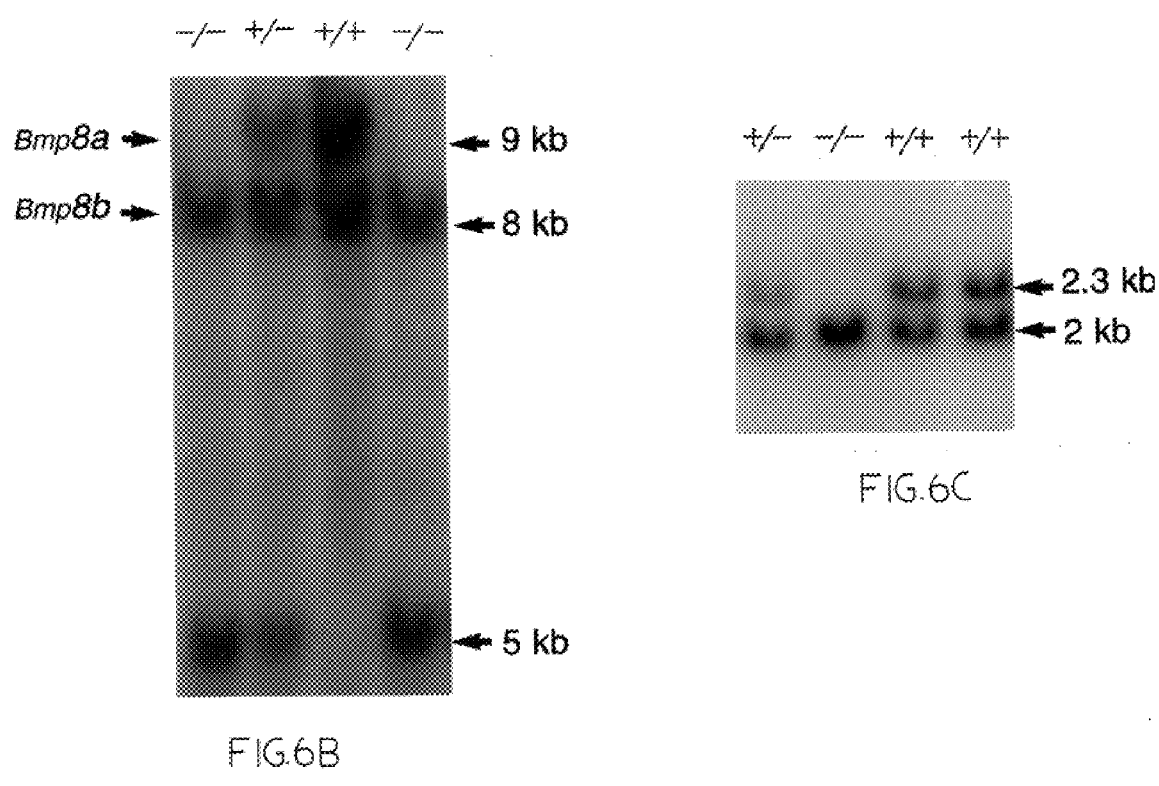

Genomic DNA was digested with EcoRI and size fractionated on a 0.8% agarose gel. Denatured DNA was then transferred to positively charged Nylon membrane and hybridized with two different probes. A 5' external Bmp8a cDNA probe, containing exons 2 and 3, hybridized to 9.0 kb and 8.0 kb bands from the wild-type Bmp8a and Bmp8b alleles, respectively, and to a 5.0 kb band from the Bmp8$^{atm1blh}$ allele (FIG. 6B). A 3' internal cDNA probe, containing exons 4, 5, 6, and 7, hybridized with 2.0 kb and 2.3 kb bands for the wild-type Bmp8a allele and only a 2.0 kb band for the Bmp8$^{atm1blh}$ allele (FIG. 6C).

Histology and in situ Hybridization

For histology, freshly dissected testes were weighed and rinsed in phosphate buffered saline (PBS), then fixed either in Bouin's fixative or in 4% paraformaldehyde-PBS for 2–24 hours depending on the size. Sections of 7 μm were mounted onto superfrost plus slides and stained either by hematoxylin/eosin or periodic acid-Schiffs reagent/ hematoxylin. Histological analysis of Bmp8b mutants and the initial survey of Bmp8a mutants in this study established that the testes from a single animal, when comparable in weight, usually have a similar histology. Therefore, only one testis from each animal was embedded and sectioned for most of the histological analysis. Testes of different genotypes were embedded and sectioned in the same block and stained on the same slides as internal controls. A third of the sections through the whole testes were mounted and stained by taking every third pair of sections for microscopic examination. If any abnormalities were observed in any given section, then the adjacent sections were mounted and stained for further examination. Seminiferous tubules that lack germ cells, or with no spermiogenesis or obviously compromised spermiogenesis, were considered abnormal. A seminiferous tubule was also scored as a degenerating tubule if it contained more than 50 germ cells with condensed nuclei and eosinophilic cytoplasm (this was considered to be characteristic of apoptosis) in 10 consecutive sections. Of the testes examined, 47% (15/32) of the Bmp8a homozygous and 17% (3/18) of the Bmp8a heterozygous mutants, and none (0/11) of the wild-type animals showed different degrees of germ cell degeneration.

In situ hybridization was performed as described herein being mindful of the following points. In brief, proteinase K treatment was extended from 7 minutes to 8 minutes for better penetrance of the probes. Hybridization temperature was raised to 60–65° C. to increase the ratio of signal/ background. High stringency washes were performed at 63° C. Slides were exposed for 10 days after being dipped in NBT2 emulsion.

The results of this set of experiments are now described.

Targeted mutagenesis of the mouse Bmp8a gene

The mouse Bmp8a gene contains seven coding exons and extends over 27 kilobases of DNA. Exons 1, 2, 3, and the first half of exon 4 encode the signal peptide and the pro-region of the precursor protein, while the second half of exon 4, and exons 5, 6, and 7 encode the mature region (Ozkaynak et al., supra). As shown in FIG. 6, in the Bmp8$^{atm1blh}$ allele, an 8-kb genomic DNA fragment encompassing exons 4, 5, and 6 is deleted and replaced by a PGK-neo$^r$ cassette (Rudnicki et al., supra) in the opposite transcriptional orientation. Therefore, DNA encoding part of the pro-region, the dibasic cleavage site RXXR, and the majority of the mature region is removed from the mouse genome. Furthermore, the remaining exons 3 and 7 are not in frame if alternative splicing of the PGK-neo$^r$ cassette should occur. It is therefore predicted that no functional or dominant negative forms of BMP8A protein will be made from the Bmp8$^{atm1blh}$ allele. In situ hybridization with $^{35}$S-labeled riboprobes against the specific 3' untranslated region of Bmp8a facilitates detection of a transcript in stage 6–8 round spermatids of homozygous mutant testis.

After drug selection, three recombinant Bmp8a mutant ES cell lines A5, H4, and H9 were obtained and injected into C57BL/6 blastocysts to generate chimeras. The Bmp8$^{atm1blh}$ allele was transmitted to offspring in lines A5 and H4. Mutant mice from both ES cell lines exhibit similar phenotypes when maintained on a mixed genetic background of [129 X Black Swiss] for this study. All data reported here were generated from a combination of these two lines.

Reproductive Performance of Bmp8a Mutants

Bmp8a is expressed in the deciduum during pregnancy, in spermatogonia and primary spermatocytes during the initiation of spermatogenesis, and in stage 6–8 round spermatids during the maintenance of spermatogenesis. This expression pattern raises the possibility that the absence of a functional Bmp8a gene would compromise the reproductive performance of both males and females. During initial mating tests of heterozygous Bmp8$^{atm1blh}$ mutants, the expected ratio of wild-type (n=45), heterozygous (n=104), and homozygous mutant (n=52) offspring was obtained. The homozygous mutants grow normally to adulthood and appear healthy. Therefore, Bmp8a is not required for embryonic and post-natal development. The fertility of the homozygous Bmp8$^{atm1blh}$ animals was further tested by mating with wild-type and heterozygous animals. As summarized in Table 1, all homozygous mutant females exhibited normal reproductive performance. All mutant males exhibited normal fertility initially. However, as they aged, some animals (2 out of 16) eventually became sterile. Therefore, Bmp8a plays a role in the fertility of certain males, but not of females.

TABLE 1

Mating Test of Bmp8a$^{tm1blh}$ mice

| Genotype | | | Litter size |
|---|---|---|---|
| Male (n) | Female (n) | Litter Number | (mean ± S.E.) |
| +/+ (3) | –/– (18) | 30 | 8.5 ± 2.2 |
| +/– (3) | | | |
| +/– (11) | +/– (23) | 77 | 8.3 ± 2.6 |
| +/– (8)* | –/– (22) | 85 | 8.1 ± 2.6 |
| –/– (8)# | +/– (20) | 66 | 8.3 ± 2.8 |
| | +/+ (5) | | |
| Comp (6)@ | +/+ (10) | 27 | 7.4 ± 3.2 |
| | Comp (10) | | |

In Table 1, 7–10 week old mice of different genotypes were caged together for 9–20 weeks. Each male was housed with 2–4 females, and pregnant females were separated before giving birth. The number of pups was recorded within 24 hours after birth. Most matings resulted in litters of normal frequency and size (wild type mating gave an average litter size of 8–8.5 pups). *One male in this group had two litters of 7–8 pups during the initial mating period, but was infertile thereafter, presumably due to epididymis degeneration and granuloma formation (FIG. 11B). #One male in this group never reproduced and histology revealed severely compromised spermiogenesis. @Comp for Bmp8 compound heterozygotes. In this group, one male never reproduced and a cyst was found in the left testis. Another male had normal reproductive performance for 8–9 weeks, but did not reproduce for the last 6 weeks. Histological examination revealed epididymis degeneration and granuloma formation (FIG. 11C).

Bmp8a is Not Required for the Initiation of spermatogenesis

Figure 7:
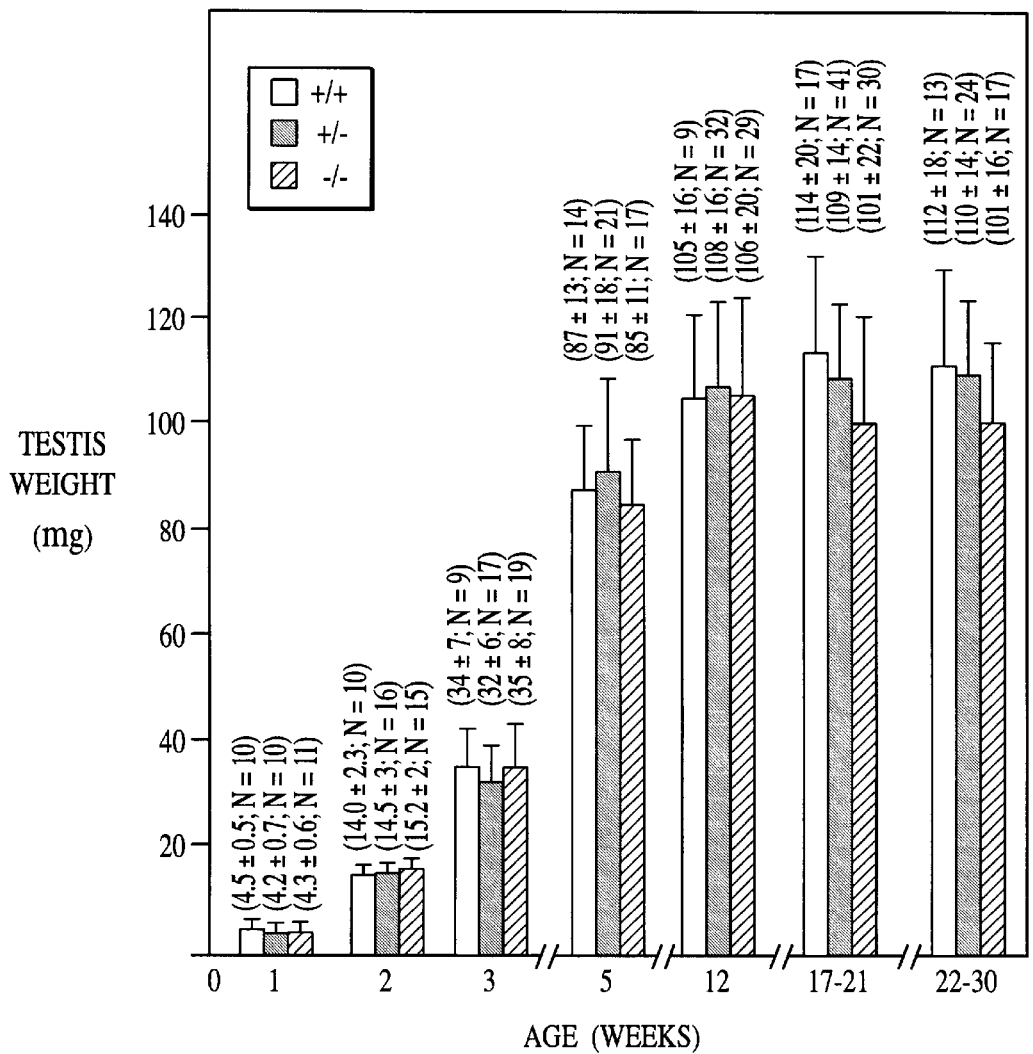
FIG. 7 is a graph depicting a comparison of testis weight between wild-type (+/+) and Bmp8$^{tm1blh}$ mutant (+/− and −/−) mice. Testes from each age group were dissected out, blotted, and weighed. Several litters were used for each group. Mean±S.E. is indicated in brackets; N represents the total number of testes in each group. Generally, one testis from each animal was weighed if the sizes of both testes appeared comparable. If in a very few cases, the size of the two testes appeared significantly different, both were weighed and the average was used for statistical analysis.
Figure 8E:
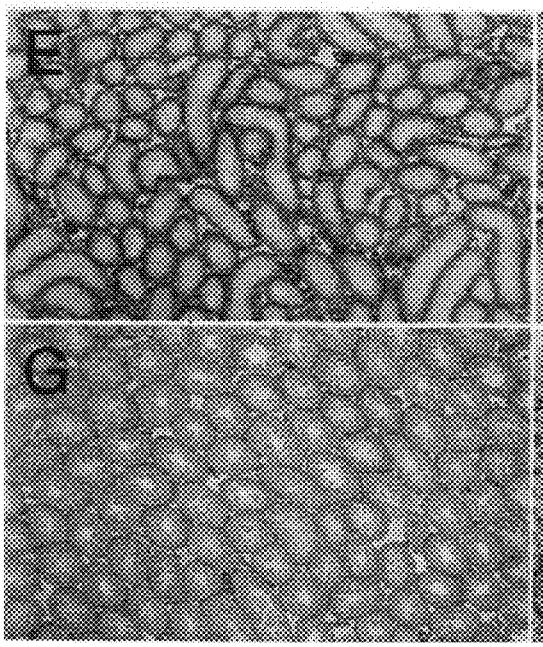
Figure 8F:
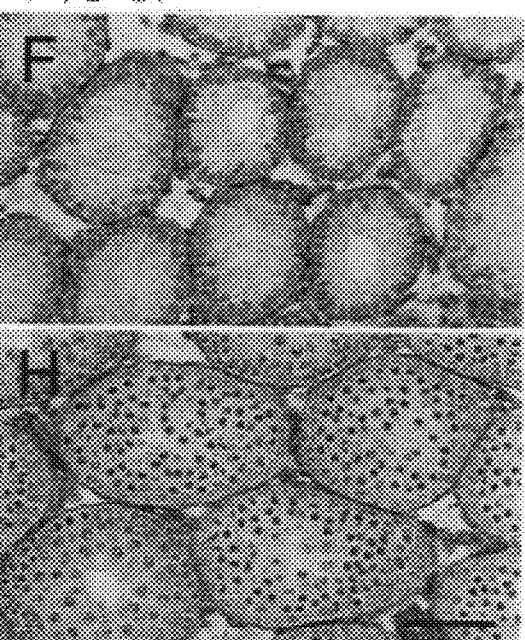
Figure 8G:
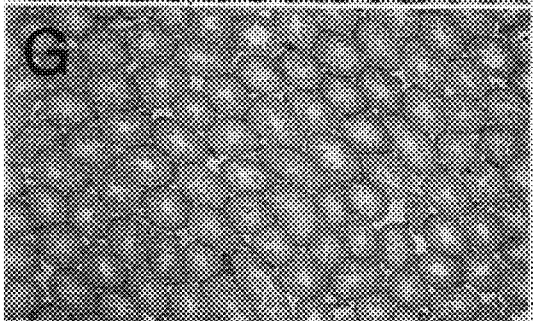
Figure 8H:
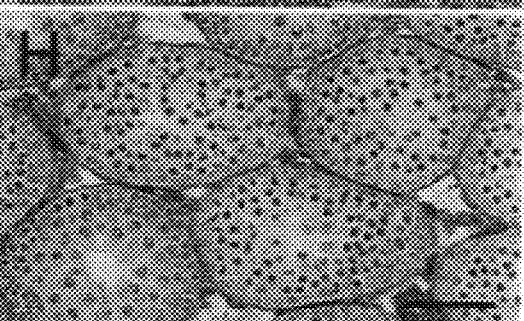
Figure 9A:
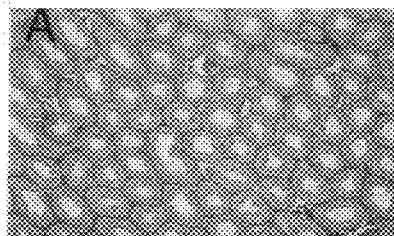
FIGS. 9A–9F, is a series of images depicting a histological comparison of wild-type (FIGS. 9A and 9B) and Bmp8a (FIGS. 9C and 9D) and Bmp8b (FIGS. 9E and 9F) homozygous mutant testes depicting the most advanced germ cell degeneration observed.
Figure 9B:
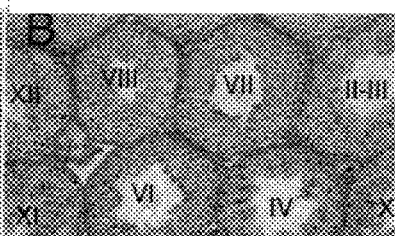
Figure 9C:
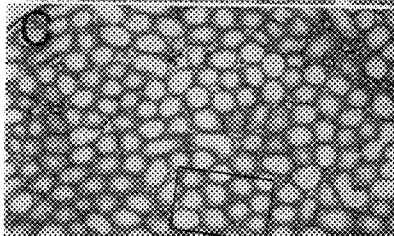
Figure 9D:
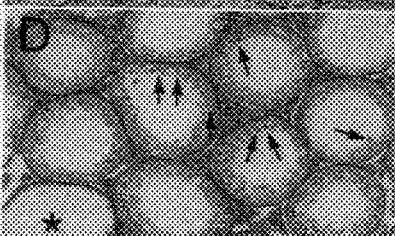
Figure 9E:
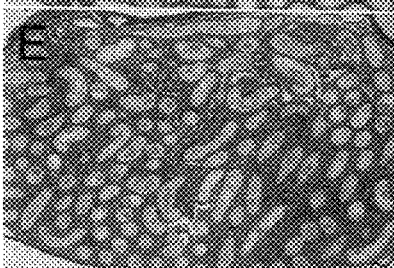
Figure 9F:
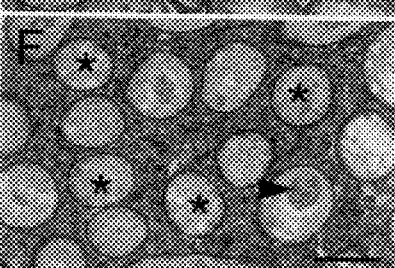

As shown in FIG. 7, from 1 week after birth to young adulthood, there was no significant difference in the average weight of testes of wild-type males compared to heterozygous or homozygous Bmp8$^{atm1blh}$ mutants. This is in contrast to the findings in Bmp8b mutants, where testes of all homozygotes from 1 to 3 weeks of age are significantly smaller than those of wild-type. Only 1 out of 30 Bmp8a homozygous mutants examined at 2 weeks of age had a small testis weighing 7 mg. This testis and 14 more testes were from Bmp8alBmp8b compound heterozygous matings and not used for the statistical analysis depicted FIG. 7. The average weight of testis from 2 week-old normal mice is 12–15 mg. The 7 mg testis had a histology similar to that of Bmp8b homozygous mutants (FIG. 8C and 8D). The testes of the remaining Bmp8a homozygous mutants at 2 weeks of age exhibited a histology similar to that of wild type mice, and no other mice with small testes were found in any other age group before puberty (6 weeks of age). In summary, histological examination of testes of more than 60 homozygous Bmp8a mutant animals (at least 10 for each age group) revealed no obvious abnormalities from 1 to 6 weeks of age (except for the one cited above).

As shown in FIG. 8, histological comparison of wild-type, Bmp8a and Bmp8b homozygous mutant, and Bmp8alBmp8b compound heterozygous testes at two weeks of age, revealed an obvious germ cell deficiency only in the Bmp8b mutant testis. Therefore, it appears that Bmp8a is not required for the initiation of spermatogenesis in the mouse.

Bmp8a Plays a Role in the Maintenance of Spermatogenesis

Based on testis weight and histology, homozygous Bmp8a mutants do not show any obvious abnormalities during the initiation of spermatogenesis. However, the testis weight of some Bmp8a mutants older than 17 weeks of age appears to be smaller than that of wild-type and heterozygous mice (FIG. 7). Although the difference of the average testis weights of wild-type and homozygous mutant testes are not statistically significant by Student's t test (P is between 0.05 and 0.1), a larger proportion of testes in the Bmp8a homozygous mutant group (13 out of 57) are below 90 mg compared to either wild-type (1 out 37) or heterozygous testes (5/86).

Histologically, about 47% (15 out of 32 testes examined of Bmp8a homozygous mutant testes from 12–30 week-old males show varied degrees of germ cell degeneration (FIGS. 9 and 10). As shown in FIGS. 9C and 9D, the most severe germ cell deficiency so far observed among the homozygous Bmp8a mutants (2 out of the 32 examined) is much milder than that seen in homozygous Bmp8b mutants (FIGS. 9E and 9F). In a majority of seminiferous tubules of such Bmp8a mutant testes, spermiogenesis (the maturation of spermatids) is severely compromised, or even absent. However, spermatogenesis (although abnormal) is still present. Increased meiotic germ cell apoptosis can be identified in most tubules, as revealed by condensed and darkly stained nuclei (arrows in FIG. 9D).

In the cases of milder forms of germ cell deficiency, only a certain percentage of the seminiferous tubules (from one tubule to 50% of the tubules) of given sections show seminiferous tubule degeneration, predominantly caused by meiotic germ cell apoptosis, resulting in the absence of spermiogenesis (FIGS. 10D–10O). These defects are similar to many of the abnormalities associated with the Bmp8b homozygous mutant phenotype. The characteristics of the apoptotic germ cells are condensed and darkly stained nuclei or chromatin and strongly eosinophilic cytoplasm. These cells can be labeled positively by TUNEL (Zhao et al., 1996, Genes and Dev. 10:1657–1669; Furuchi et al., 1996, Development 122:1703–1709; Dix et al., 1996, Proc. Natl. Acad. Sci. USA 93:3264–3268; Gavrieli et al., 1992, J. Cell. Biol. 119:493–501. Similar abnormalities are also observed in 17% of the Bmp8a heterozygous mutant testes (3 out of 18 examined). Of the Bmp8a /Bmp8b compound heterozygous mutant adult males examined, about half of them (5 out of 11) exhibit a similar germ cell degeneration phenotype.

Bmp8a Plays a Role in the Maintenance of Epididymis Integrity

As shown in Table 1, most of the Bmp8a homozygous mutant males show normal reproductive performance. However, one out of the 16 males tested was fertile within the first month, but produced no offspring afterwards. This animal was sacrificed at 4 months of age, revealing two adhesive clumps attached to the right epididymis, one attached to the caput, the other to the cauda. No obvious abnormality was found in the left testis and epididymis. Histological examination revealed gross abnormalities in the morphology of the right epididymis. As shown in FIG. 11B and 11E, a large granuloma-like mass, with sperm and some necrosis in the center and massive leukocyte infiltration on the periphery, almost replaced the cauda epididymis. Only sparsely dispersed abnormal epididymis tubules were observed outside of the granuloma mass. Subsequently, similar but milder pathological abnormalities were observed in another mating homozygous Bmp8a mutant and a Bmp8a /Bmp8b compound heterozygote (FIG. 11C, 11D, 11F, and 11G).

One interpretation of the phenotype is that the epithelium lining the epididymal tubules degenerated and sperm was forced out from the collapsed tubule. Due to the antigenicity of sperm, massive leukocyte infiltration would then accompany the eruption of the epididymal tubule, resulting in a granuloma-like mass. Similar degeneration of the epithelium and leukocyte infiltration was also found in the distal caput region of the same epididymides shown in FIG. 11B and 11C. However, in contrast to the mating group (2 out of 16 for Bmp8a homozygous mutants, 1 out of 6 for Bmp8a /Bmp8b compound heterozygous mutants), no granuloma-like pathology was found in the epididymis of more than 60 non-mating Bmp8a homozygous and Bmp8 compound heterozygous males were examined. Only epithelial degeneration was found in the distal caput region in 2 out of the 40 epididymides sectioned (FIG. 11H–11J), and no obvious epididymal epithelium degeneration was found in the cauda region of the same epididymides. Therefore, it appeared that mating exacerbated the epididymal degeneration phenotype of Bmp8a homozygous and Bmp8 compound heterozygous mutants.

Bmp8a and Bmp7 are Expressed in the Initial Segment of the Caput Epididymis

Figure 12A:
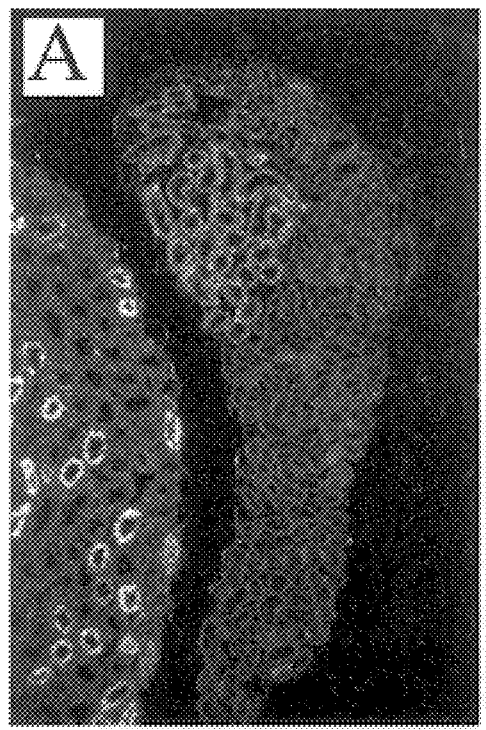
FIGS. 12A–12D, is a series of images depicting in situ hybridization depicting Bmp8a (FIGS. 12A and 12B) and Bmp7 (FIGS. 12C and 12D) expression in the epididymides of adult animals.
Figure 12B:
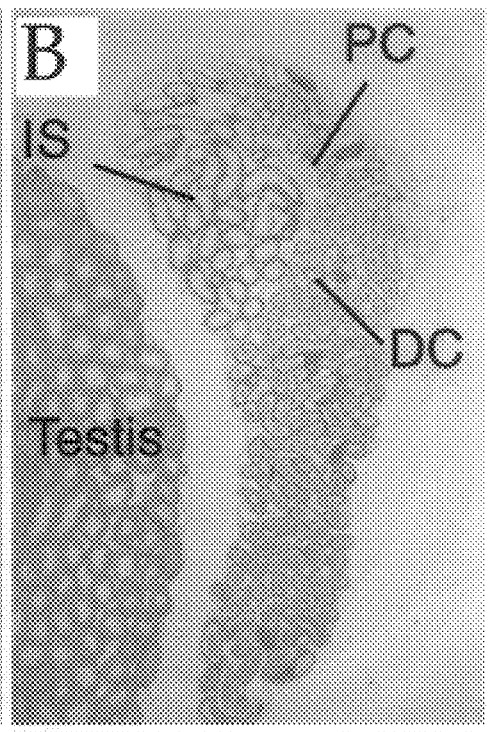
Figure 12C:
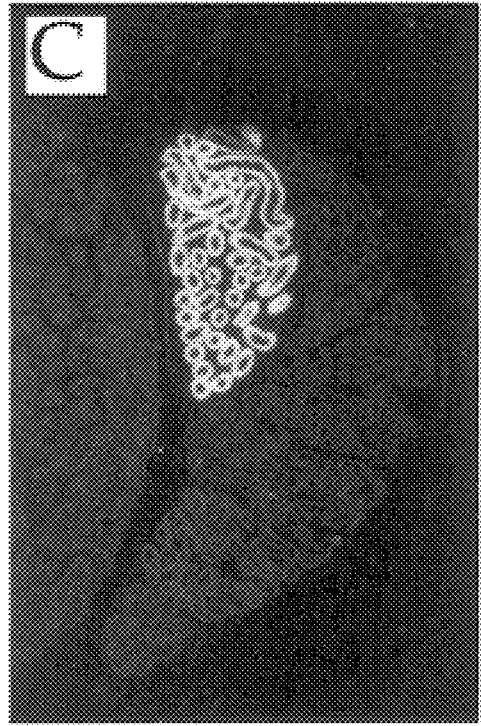
Figure 12D:
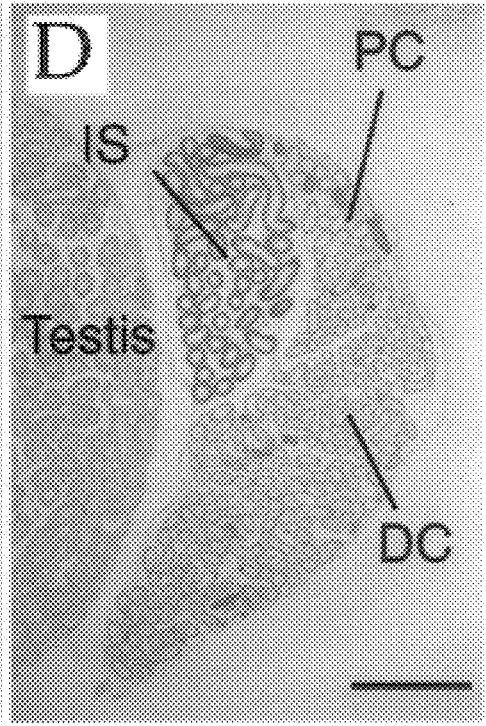

In light of the degeneration of the epididymal epithelium and granuloma formation in the Bmp8a homozygous and Bmp8a/Bmp8b compound heterozygous mutants, the expression of Bmp family members was examined in the adult epididymis of mating and non-mating animals (14–17 weeks of age). Among the genes examined (Bmp2, 4, 5, 6, 7, 8a, 8b, and Vgr2), only Bmp8a and Bmp7 exhibited significant expression. As shown in FIG. 12, both Bmp8a and Bmp7 are expressed in the same region of the epididymis, namely the initial segment of the caput. However, the expression levels of Bmp8a in this region are significantly lower than in the stage 68 round spermatids of the testis (FIG. 12A). Also, the levels of Bmp7 expression in the initial segment are much higher than those of Bmp8a.

The data just described establish that Bmp8a does not play a major role in the initiation of spermatogenesis. Further, the data establish that Bmp8a plays a role in the maintenance of spermatogenesis.

The disclosures of each and every patent, patent application and publication cited herein are hereby incorporated herein by reference in their entirety.

While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A method of proliferating mammalian spermatogonial stem cells, consisting of culturing spermatogonial stem cells with a growth factor wherein said growth factor is bone morphogenetic protein 8 to effect proliferation of said cells, wherein said fragment adequately supports survival of spermatocytes in culture.

2. The method of claim 1, wherein said bone morphogenetic protein 8 is selected from the group consisting of at least one of mouse bone morphogenetic protein 8A, mouse bone morphogenetic protein 8B, human bone morphogenetic protein 8, rat bone morphogenetic protein 8, rabbit bone morphogenetic protein 8, guinea pig bone morphogenetic protein 8, goat bone morphogenetic protein 8, pig bone morphogenetic 8, bovine bone morphogenetic protein 8, and a dimer of the C-terminal TGFβ-like portion of bone morphogenetic protein 8.

3. The method of claim 1, wherein said mammalian spermatogonial cells are selected from the group consisting of mouse, human, rat, rabbit, guinea pig, goat, pig and bovine cells.

4. A method of extending viability of a mammalian spermatogonial cell population, consisting of culturing said spermatogonial cell population with a growth factor wherein said growth factor is bone morphogenetic protein 8 wherein said fragment adequately supports survival of spermatocytes in culture, thereby extending the viability of said cultured spermatogonial cell population.

5. The method of claim 4, wherein said bone morphogenetic protein 8 is selected from the group consisting of at least one of mouse bone morphogenetic 8A, mouse bone morphogenetic protein 8B, human bone morphogenetic protein 8, rat bone morphogenetic protein 8, rabbit bone morphogenetic protein 8, guinea pig bone morphogenetic protein 8, goat bone morphogenetic protein 8, pig bone morphogenetic protein 8, bovine bone morphogenetic protein 8, and dimer of the C-terminal TGFβ-like portion of bone morphogenetic protein 8.

6. The method of claim 4, wherein said mammalian spermatogonial cells are selected from the group consisting of mouse, human, rat rabbit, guinea pig, goat, pig and bovine cells.

7. A method of selectively obtaining a proliferating population of spermatogonial stem cells in culture, consisting of adding a growth factor wherein said growth factor is bone morphogenetic protein 8 to said population of cells, wherein said fragment adequately supports survival of spermatocytes in culture, thereby selectively obtaining a proliferating population of spermatogonial stem cells.

8. The method of claim 7, wherein said bone morphogenetic protein 8 is selected from the group consisting of at least one of mouse bone morphogenetic protein 8A, mouse bone morphogenetic protein 8B, human bone morphogenetic protein 8, rat bone morphogenetic protein 8, rabbit bone morphogenetic protein 8, guinea pig bone morphogenetic protein 8, goat bone morphogenetic protein 8, pig bone morphogenetic protein 8, bovine bone morphogenetic protein 8, and a dimer of the C-terminal TGFβ-like portion of bone morphogenetic protein 8.

9. The method of claim 7, wherein said mammalian spermatogonial cells are selected from the group consisting of mouse, human, rat rabbit, guinea pig, goat, pig and bovine cells.

* * * * *

```
                              SEQUENCE LISTING (1) GENERAL INFORMATION:

(iii) NUMBER OF SEQUENCES: 4

(2) INFORMATION FOR SEQ ID NO:1:

(i) SEQUENCE CHARACTERISTICS:
          (A) LENGTH: 1917 base pairs
          (B) TYPE: nucleic acid
          (C) STRANDEDNESS: double
          (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:1:

GCCAGGCACA GGTGCGCCGT CTGGTCCTCC CCGTCTGGCG TCAGCCGAGC CCGACCAGCT      60

ACCAGTGGAT GCGCGCCGGC TGAAAGTCCG AGATGGCTAT GCGTCCCGGG CCACTCTGGC     120

TATTGGGCCT TGCTCTGTGC GCGCTGGGAG GCGGCCACGG TCCGCGTCCC CCGCACACCT     180

GTCCCCAGCG TCGCCTGGGA GCGCGCGAGC GCCGCGACAT GCAGCGTGAA ATCCTGGCGG     240

TGCTCGGGCT ACCGGGACGG CCCCGACCCC GTGCACAACC CGCCGCTGCC CGGCAGCCAG     300

CGTCCGCGCC CCTCTTCATG TTGGACCTAT ACCACGCCAT GACCGATGAC GACGACGGCG     360

GGCCACCACA GGCTCACTTA GGCCGTGCCG ACCTGGTCAT GAGCTTCGTC AACATGGTGG     420

AACGCGACCG TACCCTGGGC TACCAGGAGC CACACTGGAA GGAATTCCAC TTTGACCTAA     480

CCCAGATCCC TGCTGGGGAG GCTGTCACAG CTGCTGAGTT CCGGATCTAC AAAGAACCCA     540

GCACCCACCC GCTCAACACA ACCCTCCACA TCAGCATGTT CGAAGTGGTC CAAGAGCACT     600

CCAACAGGGA GTCTGACTTG TTCTTTTTGG ATCTTCAGAC GCTCCGATCT GGGGACGAGG     660

GCTGGCTGGT GCTGGACATC ACAGCAGCCA GTGACCGATG GCTGCTGAAC CATCACAAGG     720

ACCTGGGACT CCGCCTCTAT GTGGAAACCG CGGATGGGCA CAGCATGGAT CCTGGCCTGG     780

CTGGTCTGCT TGGACGACAA GCACCACGCT CCAGACAGCC TTTCATGGTA ACCTTCTTCA     840

GGGCCAGCCA GAGTCCTGTG CGGGCCCCTC GGGCAGCGAG ACCACTGAAG AGGAGGCAGC     900

CAAAGAAAAC GAACGAGCTT CCGCACCCCA ACAAACTCCC AGGGATCTTT GATGATGGCC     960

ACGGTTCCCG CGGCAGAGAG GTTTGCCGCA GGCATGAGCT CTACGTCAGC TTCCGTGACC    1020

TTGGCTGGCT GGACTGGGTC ATCGCCCCCC AGGGCTACTC TGCCTATTAC TGTGAGGGGG    1080

AGTGTGCTTT CCCCACTGGA CTCCTGTATGA ACGCCACCAA CCATGCCATC TTGCAGTCTC    1140

TGGTGCACCT GATGAAGCCA GATGTTGTCC CCAAGGCATG CTGTGCACCC ACCAAACTGA    1200

GTGCCACCTC TGTGCTGTAC TATGACAGCA GCAACAATGT CATCCTGCGT AAACACCGTA    1260

ACATGGTGGT CAAGGCCTGT GGCTGCCACT GAGGCCCCGC CCAGCATCCT GCTTCTACTA    1320

CCTTACCATC TGGCCGGGCC CCTCTCCAGA GGCAGAAACC CTTCTATGTT ATCATAGCTC    1380
```

```
AGACAGGGGC AATGGGAGGC CCTTCACTTC CCCTGGCCAC TTCCTGCTAA AATTCTGGTC   1440

TTTCCCAGTT CCTCTGTCCT TCATGGGGTT TCGGGGCTAT CACCCCGCCC TCTCCATCCT   1500

CCTACCCCAA GCATAGACTG AATGCACACA GCATCCCAGA GCTATGCTAA CTGAGAGGTC   1560

TGGGGTCAGC ACTGAAGGCC CACATGAGGA AGACTGATCC TTGGCCATCC TCAGCCCACA   1620

ATGGCAAATT CTGGATGGTC TAAGAAGCCC TGGAATTCTA AACTAGATGA TCTGGGCTCT   1680

CTGCACCATT CATTGTGGCA GTTGGGACAT TTTTAGGTAT AACAGACACA TACACTTAGA   1740

TCAATGCATC GCTGTACTCC TTGAAATCAG AGCTAGCTTG TTAGAAAAAG AATCAGAGCC   1800

AGGTATAGCG GTGCATGTCA TTAATCCCAG CGCTAAAGAG ACAGAGACAG GAGAATCTCT   1860

GTGAGTTCAA GGCCACATAG AAAGAGCCTG TCTCGGGAGC AGGAAAAAAA AAAAAAA     1917
```

(2) INFORMATION FOR SEQ ID NO:2:

(i) SEQUENCE CHARACTERISTICS:
        (A) LENGTH: 399 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:2:

```
Met Ala Met Arg Pro Gly Pro Leu Trp Leu Gly Leu Ala Leu Cys
1               5                   10                  15

Ala Leu Gly Gly Gly His Gly Pro Arg Pro His Thr Cys Pro Gln
                20                  25                  30

Arg Arg Leu Gly Ala Arg Glu Arg Arg Asp Met Gln Arg Glu Ile Leu
            35                  40                  45

Ala Val Leu Gly Leu Pro Gly Arg Pro Arg Pro Arg Ala Gln Pro Ala
50                  55                  60

Ala Ala Arg Gln Pro Ala Ser Ala Pro Leu Phe Met Leu Asp Leu Tyr
65                  70                  75                  80

His Ala Met Thr Asp Asp Asp Asp Gly Gly Pro Pro Gln Ala His Leu
                85                  90                  95

Gly Arg Ala Asp Leu Val Met Ser Phe Val Asn Met Val Glu Arg Asp
                100                 105                 110

Arg Thr Leu Gly Tyr Gln Glu Pro His Trp Lys Glu Phe His Phe Asp
            115                 120                 125

Leu Thr Gln Ile Pro Ala Gly Glu Ala Val Thr Ala Ala Glu Phe Arg
130                 135                 140

Ile Tyr Lys Glu Pro Ser Thr His Pro Leu Asn Thr Thr Leu His Ile
145                 150                 155                 160

Ser Met Phe Glu Val Val Gln Glu His Ser Asn Arg Glu Ser Asp Leu
                165                 170                 175

Phe Phe Leu Asp Leu Gln Thr Leu Arg Ser Gly Asp Glu Gly Trp Leu
            180                 185                 190

Val Leu Asp Ile Thr Ala Ala Ser Asp Arg Trp Leu Leu Asn His His
            195                 200                 205

Lys Asp Leu Gly Leu Arg Leu Tyr Val Glu Thr Ala Asp Gly His Ser
210                 215                 220

Met Asp Pro Gly Leu Ala Gly Leu Leu Gly Arg Gln Ala Pro Arg Ser
225                 230                 235                 240

Arg Gln Pro Phe Met Val Thr Phe Phe Arg Ala Ser Gln Ser Pro Val
                245                 250                 255
```

```
Arg Ala Pro Arg Ala Ala Arg Pro Leu Lys Arg Gln Pro Lys Lys
            260                 265                 270

Thr Asn Glu Leu Pro His Pro Asn Lys Leu Pro Gly Ile Phe Asp Asp
        275                 280                 285

Gly His Gly Ser Arg Gly Arg Glu Val Cys Arg Arg His Glu Leu Tyr
        290                 295                 300

Val Ser Phe Arg Asp Leu Gly Trp Leu Asp Trp Val Ile Ala Pro Gln
305                 310                 315                 320

Gly Tyr Ser Ala Tyr Tyr Cys Glu Gly Glu Cys Ala Phe Pro Leu Asp
                325                 330                 335

Ser Cys Met Asn Ala Thr Asn His Ala Ile Leu Gln Ser Leu Val His
            340                 345                 350

Leu Met Lys Pro Asp Val Val Pro Lys Ala Cys Cys Ala Pro Thr Lys
        355                 360                 365

Leu Ser Ala Thr Ser Val Leu Tyr Tyr Asp Ser Ser Asn Asn Val Ile
        370                 375                 380

Leu Arg Lys His Arg Asn Met Val Val Lys Ala Cys Gly Cys His
385                 390                 395
```

(2) INFORMATION FOR SEQ ID NO:3:

(i) SEQUENCE CHARACTERISTICS:
        (A) LENGTH: 2183 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:3:

```
ACACTCGCTA TTCCCTACCG CGCGGGCCCA CGTTGCTCTG CGGGACCTAC AGGCTGGCTG      60
CTGCCTGCGG ACGCGTGGAG CAGTCGTCTT AGAGCTGCCC GCGACAGGTG CGAACTCGGG     120
ATCCGCGGCG CTGTCCCATC CTTGTCGTCG AGGCGTCGCT GGATGCGAGT CCGCTAAACG     180
TCCGAGATGG CTGCGCGTCC GGGACTCCTA TGGCTACTGG GCCTGGCTCT GTGCGTGTTG     240
GGCGGCGGTC ACCTCTCGCA TCCCCCGCAC GTCTTTCCCC AGCGTCGACT AGGAGTACGC     300
GAGCCCCGCG ACATGCAGCG CGAGATTCGG GAGGTGCTGG GGCTGCCGGG GCGGCCCCGA     360
TCCCGAGCAC CGGTCGGGGC TGCCCAGCAG CCAGCGTCTG CGCCCCTCTT TATGTTGGAC     420
CTGTACCGTG CCATGACGGA TGACAGTGGC GGTGGGACCC CGCAGCCTCA CTTGGACCGT     480
GCTGACCTGA TTATGAGCTT TGTCAACATA GTGGAACGCG ACCGTACCCT GGGCTACCAG     540
GAGCCACACT GGAAGGAATT CCACTTTGAC CTAACCCAGA TCCCTGCTGG GGAGGCTGTC     600
ACAGCTGCTG AGTTCCGGAT CTACAAAGAA CCCAGTACCC ACCCGCTCAA CACAACCTTC     660
CACATCAGCA TGTTCGAAGT GGTCCAAGAG CACTCCAACA GGGAGTCTGA CTTGTCCTTT     720
TTGGATCTTC AGACGCTCCG ATCTGGGAC GAGGGCTGGC TGGTGCTGGA CATCACAGCA     780
GCCAGTGACC GATGGCTGCT GAACCATCAC AAGGACCTAG GACTCCGCCT CTATGTGGAA     840
ACCGAGGATG GCACGGCAT AGATCCTGGC CTAGCTGGTC TGCTTGGACG ACAAGCACCA     900
CGCTCCAGAC AGCCTTTCAT GGTTGGTTTC TTCAGGGCCA ACCAGAGTCC TGTGCGGGCC     960
CCTCGAACAG CAAGACCACT GAAGAAGAAG CAGCTAAATC AAATCAACCA GCTGCCGCAC    1020
```

```
TCCAACAAAC ACCTAGGAAT CCTTGATGAT GGCCACGGTT CTCACGGCAG AGAAGTTTGC      1080

CGCACAGGTG AGCTCTATGT CAGCTTCCGT GACCTTGGCT GGCTGGACTC TGTCATTGCC      1140

CCCCAGGGCT ACTCCGCCTA TTACTGTGCT GGGGAGTGCA TCTACCCACT GAACTCCTGT      1200

ATGAACTCCA CCAACCACGC CACTATGCAG GCCCTGGTAC ATCTGATGAA GCCAGATATC      1260

ATCCCCAAGG TGTGCTGTGT GCCTACTGAG CTGAGTGCCA TTTCTCTGCT CTACTATGAT      1320

AGAAACAATA ATGTCATCCT GCGCAGGGAG CGCAACATGG TAGTCCAGGC CTGTGGCTGC      1380

CACTGAGTCC CTGCCCAACA GCCTGCTGCC ATCCCATCTA TCTAGTCAGG CCTCTCTTCC      1440

AAGGCAGGAA ACCAACAAAG AGGGAAGGCA GTGCTTTCAA CTCCATGTCC ACATTTACAG      1500

TCTTGGCCCT CTCTGTTCTT TTTGCCAAGG CTGAGAGATG GTCCTAGTTA TAACCCTGGT      1560

GACCTCAGTA GCCCATCTCT CATCTCCCCA AACTCCCCCA ATGCAGCCAG GGGCATCTAT      1620

GTCCTTTGGG ATTGGCACAG AAGTCCAATT TACCAACTTA TTCATGATCA CTACTGCCCA      1680

GCCTGACTTG AACCTGGAAC ACAGGGTAGA GCTCAGGCTC TTCAGTATCC ATCAGAAGAT      1740

TTAGGTGTGT GCAGACATGA CCACACTCCC CCTAGCACTC CATAGCCTGT CTCTTGGGGG      1800

TGCAAAATGG GATTTCTAGA GAAGAGTTTA AAATATATGG AAAAGCTAGG TATAGTAATG      1860

CACACTGTAA TCTTAGCACT TGGGAAGCTG AGGCAGTTCA AGGCCAGCCT GGGATATATA      1920

TCAAGATCTC ATTCATATCT ATCTATCTAT CTATCTATCT ATCTATCTAT CTATCTATCT      1980

ATCTATCTAT CTATCTATCT CTATATATAT ATCAAGATCT TCCTTCAAAA CAAACAAAGC      2040

AAAACCCTGG TGTATTTATG GATCTCAGTC ACTAAACCTC TGCCACAGGC AGCCACAAGA      2100

GGCCAGCTAA TGAAAAAACC TATTGCGGAT TTATCATCTG GATTTAGGCA TCGTCATTAA      2160

AGAAAATGCC AACAGTTTCC CTG                                              2183
```

(2) INFORMATION FOR SEQ ID NO:4:

(i) SEQUENCE CHARACTERISTICS:
        (A) LENGTH: 399 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:4:

```
Met Ala Ala Arg Pro Gly Leu Leu Trp Leu Leu Gly Leu Ala Leu Cys
 1               5                  10                  15

Val Leu Gly Gly Gly His Leu Ser His Pro His Val Phe Pro Gln
                20                  25                  30

Arg Arg Leu Gly Val Arg Glu Pro Arg Asp Met Gln Arg Glu Ile Arg
                35                  40                  45

Glu Val Leu Gly Leu Pro Gly Arg Pro Arg Ser Arg Ala Pro Val Gly
 50                  55                  60

Ala Ala Gln Gln Pro Ala Ser Ala Pro Leu Phe Met Leu Asp Leu Tyr
 65                  70                  75                  80

Arg Ala Met Thr Asp Asp Ser Gly Gly Gly Thr Pro Gln Pro His Leu
                85                  90                  95

Asp Arg Ala Asp Leu Ile Met Ser Phe Val Asn Ile Val Glu Arg Asp
                100                 105                 110

Arg Thr Leu Gly Tyr Gln Glu Pro His Trp Lys Glu Phe His Phe Asp
            115                 120                 125

Leu Thr Gln Ile Pro Ala Gly Glu Ala Val Thr Ala Ala Glu Phe Arg
 130                 135                 140
```

```
Ile Tyr Lys Glu Pro Ser Thr His Pro Leu Asn Thr Thr Phe His Ile
145                 150                 155                 160

Ser Met Phe Glu Val Val Gln Glu His Ser Asn Arg Glu Ser Asp Leu
                165                 170                 175

Ser Phe Leu Asp Leu Gln Thr Leu Arg Ser Gly Asp Glu Gly Trp Leu
                180                 185                 190

Val Leu Asp Ile Thr Ala Ala Ser Asp Arg Trp Leu Leu Asn His His
            195                 200                 205

Lys Asp Leu Gly Leu Arg Leu Tyr Val Glu Thr Glu Asp Gly His Gly
        210                 215                 220

Ile Asp Pro Gly Leu Ala Gly Leu Leu Gly Arg Gln Ala Pro Arg Ser
225                 230                 235                 240

Arg Gln Pro Phe Met Val Gly Phe Phe Arg Ala Asn Gln Ser Pro Val
                245                 250                 255

Arg Ala Pro Arg Thr Ala Arg Pro Leu Lys Lys Lys Gln Leu Asn Gln
            260                 265                 270

Ile Asn Gln Leu Pro His Ser Asn Lys His Leu Gly Ile Leu Asp Asp
        275                 280                 285

Gly His Gly Ser His Gly Arg Glu Val Cys Arg Thr Gly Glu Leu Tyr
    290                 295                 300

Val Ser Phe Arg Asp Leu Gly Trp Leu Asp Ser Val Ile Ala Pro Gln
305                 310                 315                 320

Gly Tyr Ser Ala Tyr Tyr Cys Ala Gly Glu Cys Ile Tyr Pro Leu Asn
                325                 330                 335

Ser Cys Met Asn Ser Thr Asn His Ala Thr Met Gln Ala Leu Val His
            340                 345                 350

Leu Met Lys Pro Asp Ile Ile Pro Lys Val Cys Cys Val Pro Thr Glu
        355                 360                 365

Leu Ser Ala Ile Ser Leu Leu Tyr Tyr Asp Arg Asn Asn Asn Val Ile
    370                 375                 380

Leu Arg Arg Glu Arg Asn Met Val Val Gln Ala Cys Gly Cys His
385                 390                 395
```